United States Patent
Chin et al.

(10) Patent No.: US 9,161,842 B2
(45) Date of Patent: Oct. 20, 2015

(54) SYSTEM AND METHOD FOR AN INTERBODY SPINAL FUSION ASSEMBLY

(71) Applicant: SPINEFRONTIER, INC, Beverly, MA (US)

(72) Inventors: Kingsley R. Chin, Wilton Manors, FL (US); Lin Yin, Brighton, MA (US); Vito Lore, Somerville, MA (US); Matthew Ibarra, Lakewood, CA (US); Michael Drnek, Hampstead, NH (US)

(73) Assignee: SPINEFRONTIER, INC, Malden, MA (US)

( * ) Notice: Subject to any disclaimer, the term of this patent is extended or adjusted under 35 U.S.C. 154(b) by 191 days.

(21) Appl. No.: 14/034,378

(22) Filed: Sep. 23, 2013

(65) Prior Publication Data

US 2014/0088711 A1 Mar. 27, 2014

Related U.S. Application Data

(60) Provisional application No. 61/704,800, filed on Sep. 24, 2012.

(51) Int. Cl.
| | |
|---|---|
| *A61F 2/44* | (2006.01) |
| *A61F 2/46* | (2006.01) |
| *A61F 2/30* | (2006.01) |
| *A61B 17/80* | (2006.01) |

(52) U.S. Cl.
CPC .............. *A61F 2/447* (2013.01); *A61F 2/30749* (2013.01); *A61F 2/4455* (2013.01); *A61F 2/4611* (2013.01); *A61B 17/8033* (2013.01); *A61B 17/8052* (2013.01); *A61F 2002/305* (2013.01); *A61F 2002/30331* (2013.01); *A61F 2002/30571* (2013.01); *A61F 2002/30578* (2013.01); *A61F 2002/30579* (2013.01); *A61F 2002/30604* (2013.01); *A61F 2002/30733* (2013.01); *A61F 2002/30787* (2013.01); *A61F 2002/30878* (2013.01); *A61F 2002/30884* (2013.01); *A61F 2002/30904* (2013.01); *A61F 2002/4619* (2013.01); *A61F 2002/4627* (2013.01); *A61F 2002/4629* (2013.01)

(58) Field of Classification Search
CPC ...................................................... A61F 2/4455
See application file for complete search history.

(56) References Cited

U.S. PATENT DOCUMENTS

| | | | |
|---|---|---|---|
| 2009/0105832 A1* | 4/2009 | Allain et al. ............... | 623/17.16 |
| 2009/0157188 A1 | 6/2009 | Zeegers | |
| 2010/0087925 A1 | 4/2010 | Kostuik et al. | |
| 2011/0230971 A1* | 9/2011 | Donner et al. ............. | 623/17.16 |
| 2012/0150300 A1 | 6/2012 | Nihalani | |
| 2013/0226300 A1* | 8/2013 | Chataigner et al. ........ | 623/17.16 |
| 2014/0180417 A1* | 6/2014 | Bergey ........................ | 623/17.16 |
| 2014/0379085 A1* | 12/2014 | Duffield et al. ............ | 623/17.16 |

FOREIGN PATENT DOCUMENTS

WO WO0213732 A2 2/2002

OTHER PUBLICATIONS

International Search Report, ISA/KR, Dec. 26, 2013.

\* cited by examiner

*Primary Examiner* — Andrew Yang
(74) *Attorney, Agent, or Firm* — AKC Patents, LLC; Aliki K. Collins

(57) ABSTRACT

An interbody spinal fusion assembly includes an interbody cage, planar metal pins and bone fasteners. The interbody cage includes a metal cage and a PEEK insert. The PEEK insert is inserted into a slot of the metal cage and is secured to the metal cage with a pin. The assembled interbody cage is inserted in the space between two adjacent vertebras and is secured in placed with the planar metal pins and the bone fasteners.

22 Claims, 29 Drawing Sheets

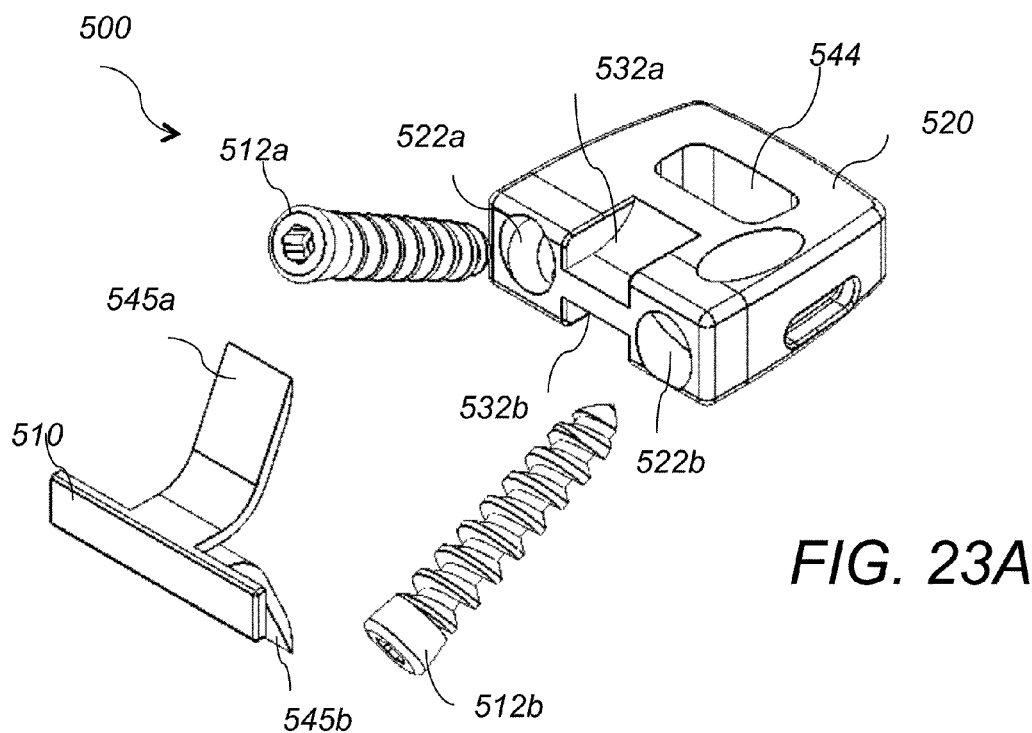
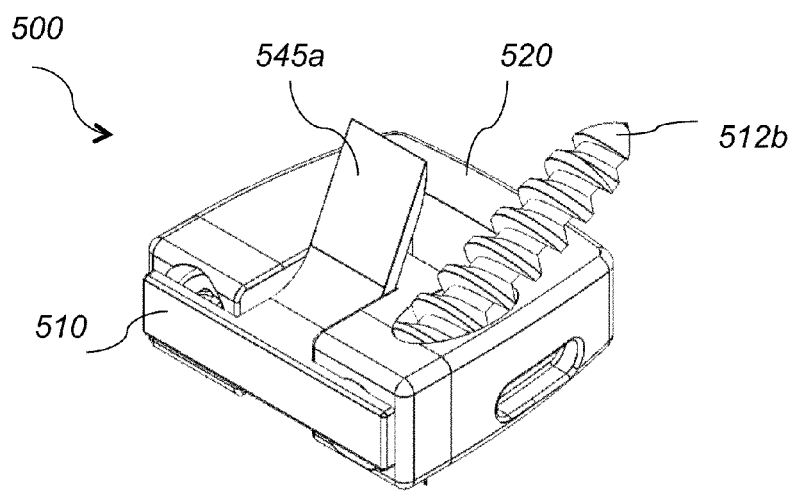
FIG. 23A
FIG. 23B

SYSTEM AND METHOD FOR AN INTERBODY SPINAL FUSION ASSEMBLY

CROSS REFERENCE TO RELATED CO-PENDING APPLICATIONS

This application claims the benefit of U.S. provisional application Ser. No. 61/704,800 filed Sep. 24, 2012 and entitled "SYSTEM AND METHOD FOR AN INTERBODY SPINAL FUSION ASSEMBLY", the contents of which are expressly incorporated herein by reference.

FIELD OF THE INVENTION

The present invention relates to a system and a method for an interbody spinal fusion assembly, and more particularly to an interbody spinal fusion assembly that includes an interbody cage, planar metal pins and bone engaging fasteners.

BACKGROUND OF THE INVENTION

Fibula strut grafts have a proven history of effectiveness for anterior cervical corpectomies but are inherently vulnerable to complications such as early or late fracture, dislodgement, displacement, telescoping into the vertebral body, or non-union. The settling and resultant segmental kyphosis after multi-level anterior cervical reconstruction have also been documented. The risk of graft migration, displacement, or fracture appears more likely with more vertebral bodies removed and longer grafts, and with corpectomies involving a fusion ending at the C7 vertebral body. Newer interbody stabilization options have emerged such as polyetherketone (PEEK) which have the advantages of greater endplate coverage leading to a more stable construct and with similar modulus of elasticity as bone. However, PEEK cages tend to move out of position and usually require separate fixation plates. Other options include metal expandable cages but these can be bulky, risk adjacent body fracture, and have limited room for bone graft, and therefore, do not provide the most ideal biologic environment.

SUMMARY OF THE INVENTION

The present invention relates to an interbody spinal fusion assembly that includes an interbody cage, planar metal pins and bone fasteners. The interbody cage includes a metal cage and a PEEK insert. The PEEK insert is inserted into a slot of the metal cage and is secured to the metal cage with a pin. The assembled interbody cage is inserted in the space between two adjacent vertebras and is secured in placed with metal planar pins and bone engaging fasteners.

In general, in one aspect, the invention features, an interbody spinal fusion assembly configured for implantation at least partially between a superior vertebra and an inferior vertebra. The interbody spinal fusion assembly includes an interbody cage that has left and right side surfaces, front and back surfaces and top and bottom surfaces. The interbody cage comprises a metal cage, a plastic insert, and first and second planar metal pins. The metal cage comprises a front slot extending from the front surface towards the center of the interbody cage and the plastic insert is shaped and dimensioned to fit within the front slot. The metal cage further comprises a back slot extending from the back surface towards the center of the interbody cage and the first and second metal pins are shaped and dimensioned to fit and sit within the back slot. The front slot does not intersect with the back slot.

Implementations of this aspect of the invention may include one or more of the following features. The back slot comprises left and right upwards curved grooves and left and right downwards curved grooves. The first and second planar metal pins comprise left and right sides that are shaped and dimensioned to slide within the left and right upwards curved grooves and the left and right downwards curved grooves, respectively, after the implantation of the interbody cage. The left and right upwards curved grooves do not intersect with the left and right downwards curved grooves. The interbody spinal fusion assembly further includes first and second bone fasteners, and the metal cage further comprises a top through opening extending from the top surface towards the bottom surface and first and second through openings starting in the back surface and extending diagonally towards the top and bottom surfaces, respectively. The first and second through opening are dimensioned to receive the first and second bone fasteners, respectively. The interbody spinal fusion assembly further includes a pin and the position of the plastic insert is secured within the front slot of the metal cage with the pin. The top and bottom surfaces of the interbody cage comprise bone engaging teeth. Each of the first and second planar metal pins comprises an elongated curved body having a trapezoid shaped front end, a rectangular through opening and a central pin. The central pin extends from the front end of the elongated curved body within the rectangular opening and comprises a distal end projecting in a direction opposite to the curvature of the elongated curved body. The metal cage further comprises top and bottom depressions on the top and bottom surfaces, respectively, and the top and bottom depressions are shaped and dimensioned to engage the distal end of the central pin of the first and second planar metal pins, respectively. The elongated curved body comprises a back portion with smooth left and right sides, a front portion with teethed left and right sides, and teeth along the left and right edges of the top surface. The metal cage comprises one of titanium, stainless steel, biocompatible metal or alloys thereof. The first and second planar metal pins comprise one of titanium, stainless steel, biocompatible metal or alloys thereof. The plastic insert comprises PEEK.

In general, in one aspect, the invention features a method for spinal stabilization including the following. First providing an interbody spinal fusion assembly comprising an interbody cage that includes left and right side surfaces, front and back surfaces and top and bottom surfaces. The interbody cage comprises a metal cage, a plastic insert, and first and second planar metal pins. The metal cage comprises a front slot extending from the front surface towards the center of the interbody cage and the plastic insert is shaped and dimensioned to fit within the front slot. The metal cage further comprises a back slot extending from the back surface towards the center of the interbody cage and the first and second planar metal pins are shaped and dimensioned to fit and sit within the back. The front slot does not intersect with the back slot. Next, inserting and implanting the interbody cage at least partially between a superior vertebra and an inferior vertebra. Next, pushing the first and second planar metal pins from within the back slot towards the front surface of the interbody cage and engaging the vertebral endplates of the superior and inferior vertebras with the first and second planar metal pins, respectively.

The details of one or more embodiments of the invention are set forth in the accompanying drawings and description below. Other features, objects, and advantages of the invention will be apparent from the following description of the preferred embodiments, the drawings, and the claims

BRIEF DESCRIPTION OF THE DRAWINGS

Referring to the figures, wherein like numerals represent like parts throughout the several views:

FIG. 23A depicts an exploded view of another embodiment of the interbody spinal fusion assembly, according to this invention; and FIG. 23B depicts the assembled interbody spinal fusion assembly of FIG. 23A.

DETAILED DESCRIPTION OF THE INVENTION

The present invention relates to an interbody spinal fusion assembly that includes an interbody cage, planar metal pins and bone fasteners. The interbody cage is inserted in the space between two adjacent vertebras and is secured in placed with metal planar pins and bone engaging fasteners.

Figure 1:
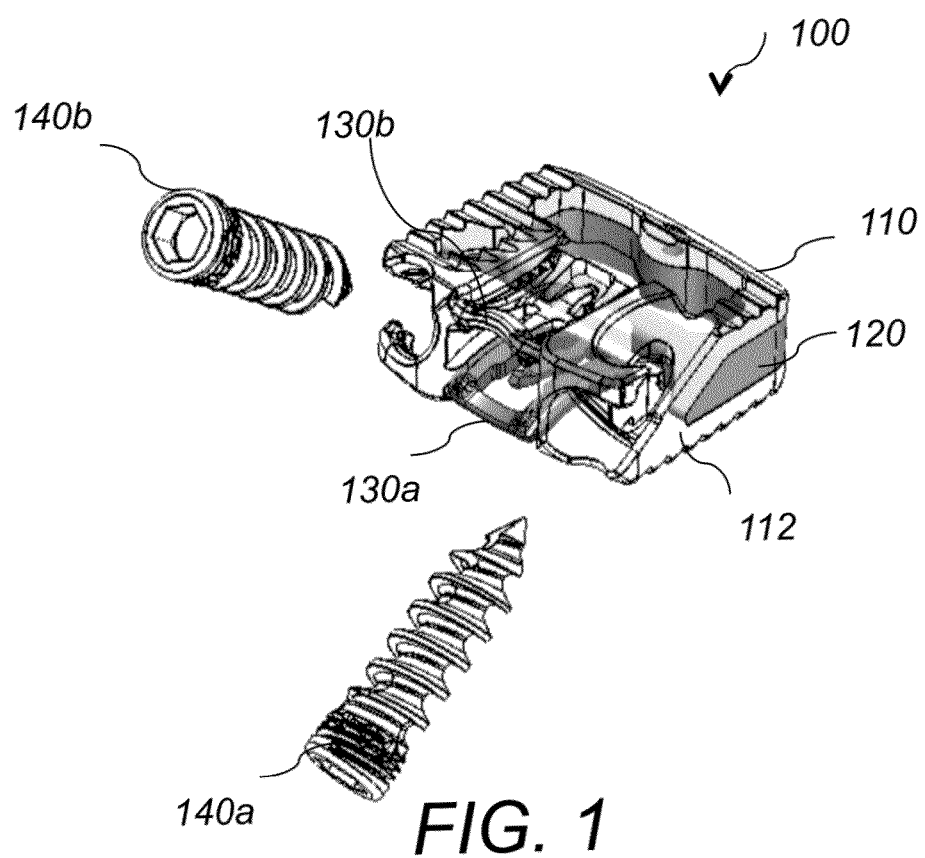
FIG. 1 is a perspective view of an interbody spinal fusion assembly in the "non-engaged position", according to this invention.
Figure 2:
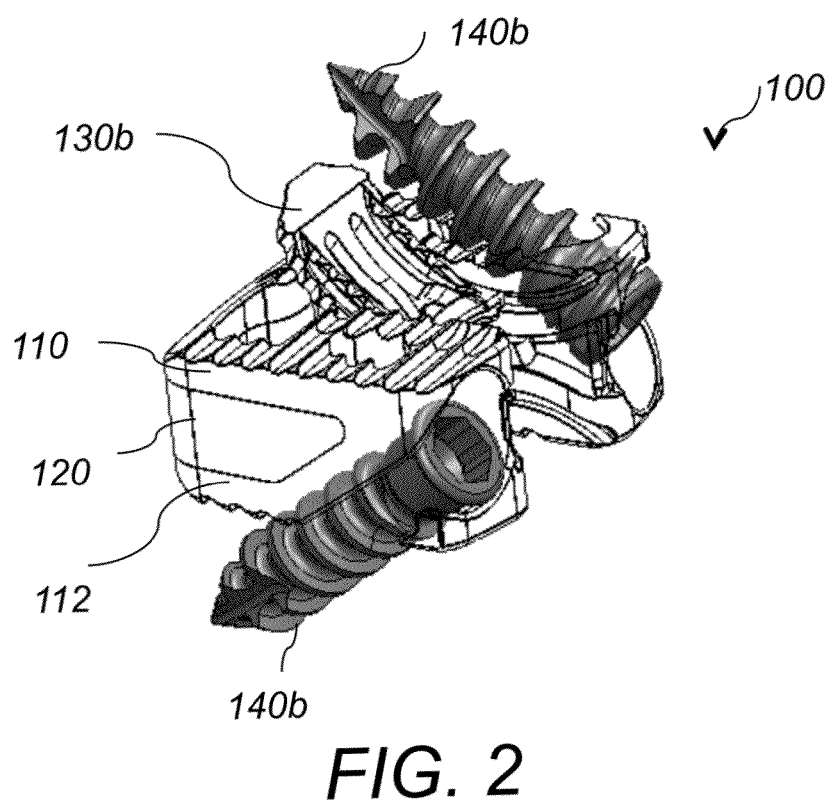
FIG. 2 is a perspective view of the interbody spinal fusion assembly of FIG. 1 in the "engaged position"
Figure 3:
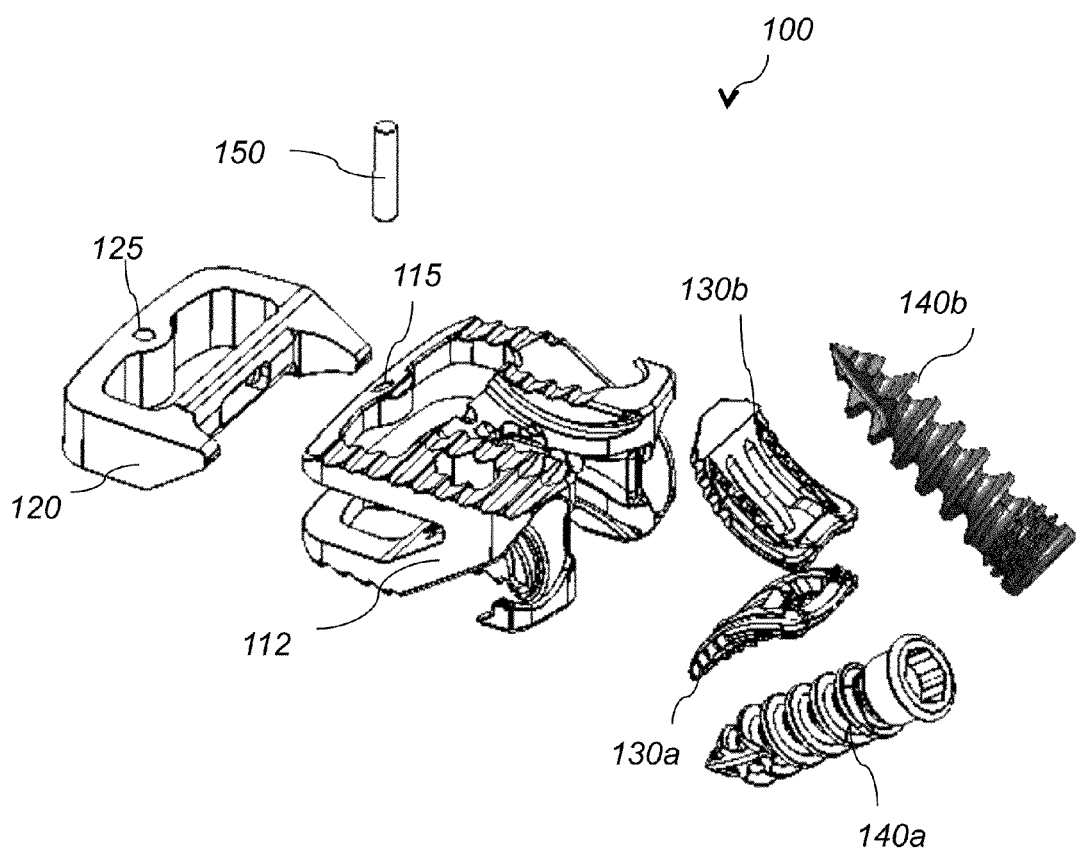
FIG. 3 is an exploded view of the interbody spinal fusion assembly of FIG. 2.
Figure 4A:
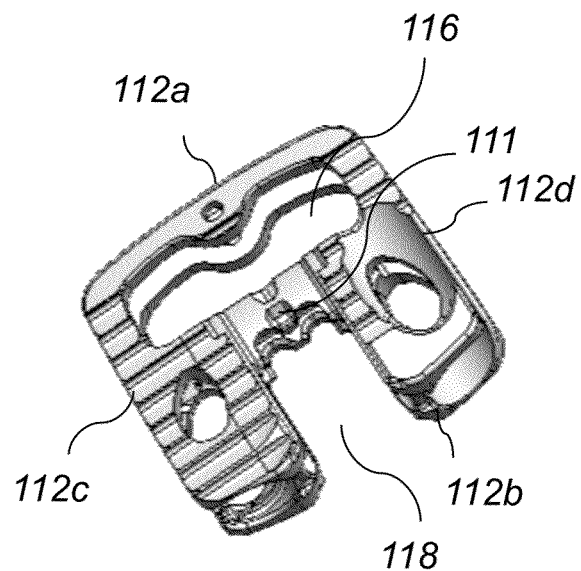
FIG. 4A is a top perspective view of the interbody cage of FIG. 3.
Figure 4B:
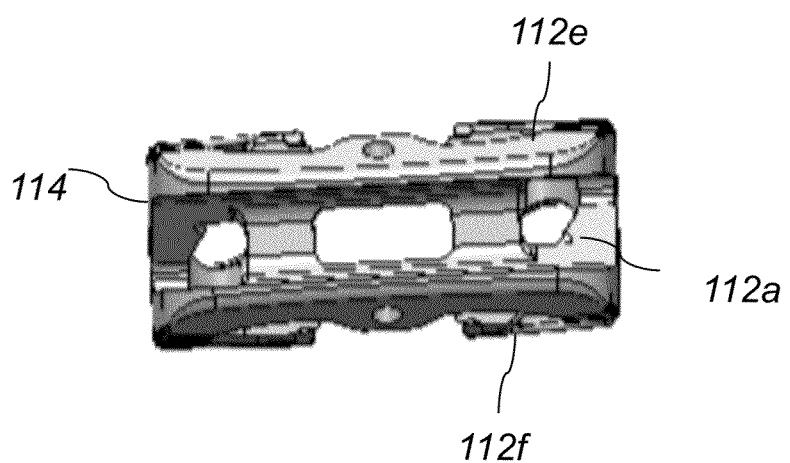
FIG. 4B is a front perspective view of the interbody cage of FIG. 3.
Figure 4C:
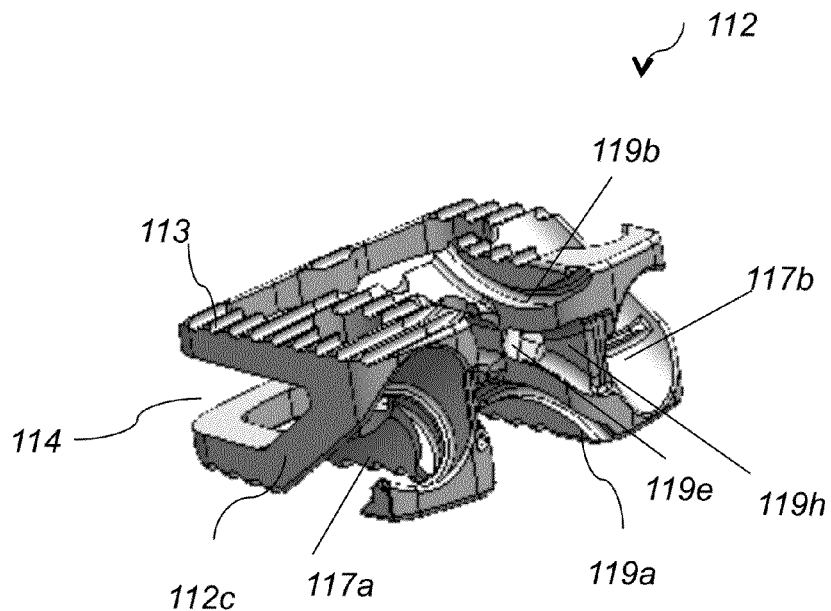
FIG. 4C is a right side perspective view of the interbody cage of FIG. 3.
Figure 4D:
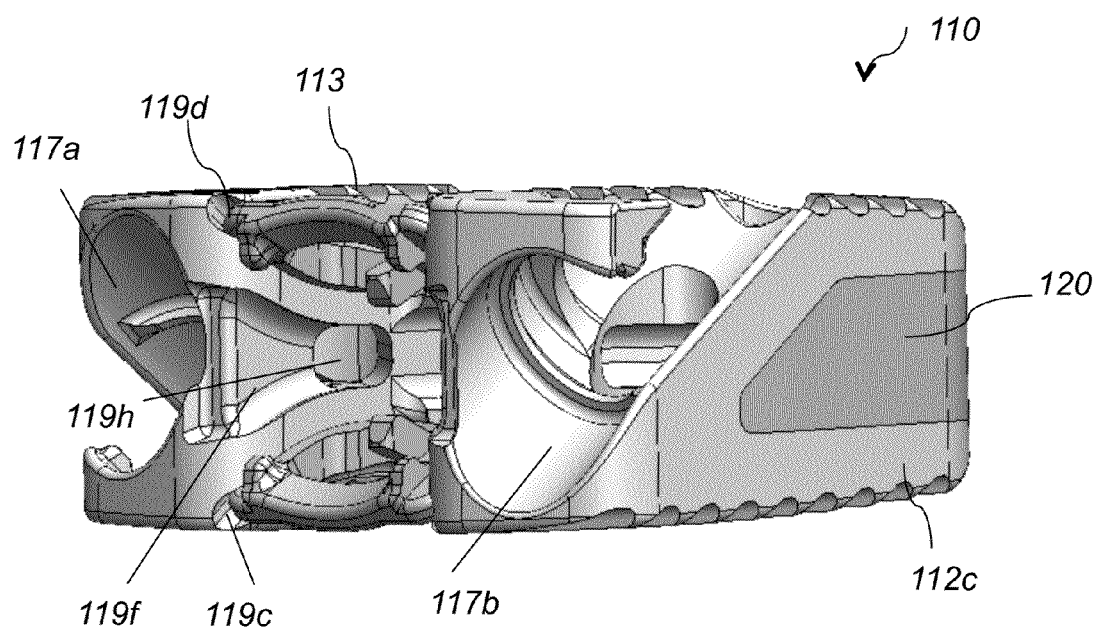
FIG. 4D is a left side perspective view of the interbody cage of FIG. 3.
Figure 5A:
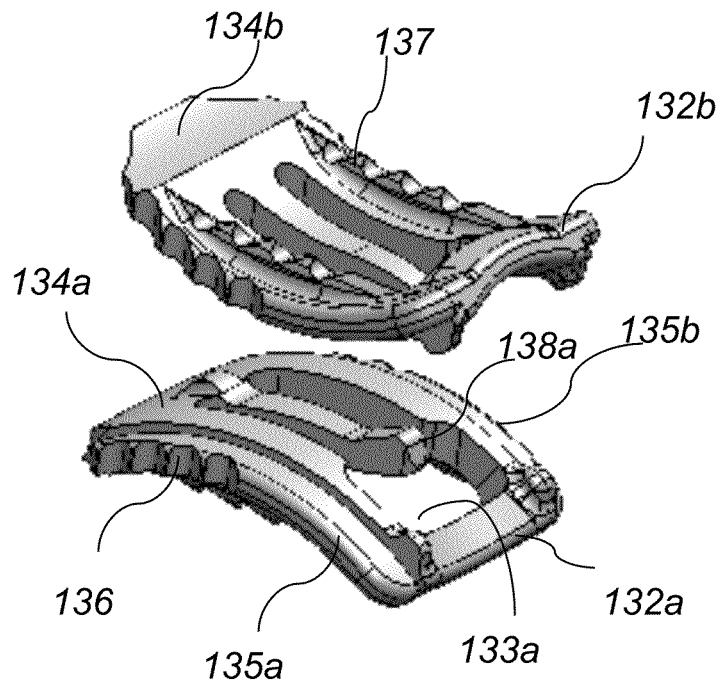
FIG. 5A is a perspective view of the planar pins of FIG. 3 in the "non-engaged" position.
Figure 5B:
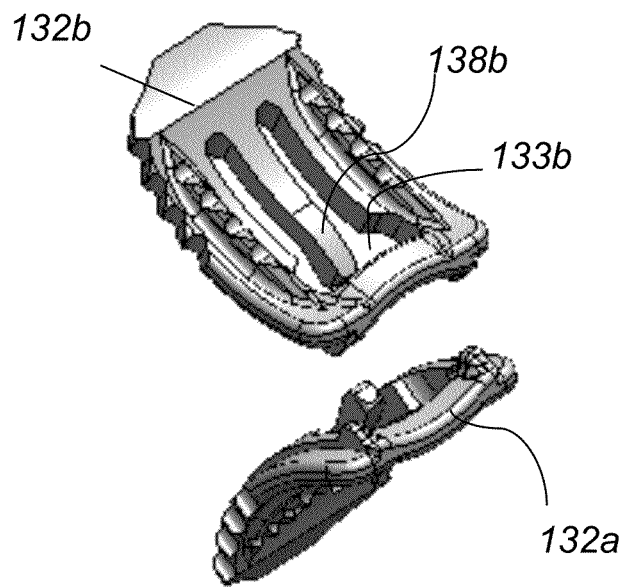
FIG. 5B is a perspective view of the planar pins of FIG. 3 in the "engaged" position.

Referring to FIG. 1, FIG. 2 and FIG. 3, interbody spinal fusion assembly 100 includes an interbody cage 110, planar pins 130a, 130b and bone engaging fasteners 140a, 140b. Interbody cage 110 includes a metal cage 112 and an insert 120. Insert 120 is made of PEEK or other plastic material and is positioned within a slot 114 formed at the front side 112a of the metal cage 112. Metal cage 112 is made of titanium, steel, or any other biocompatible metal or alloy. Insert 120 is secured to the metal cage 112 with a pin 150 positioned within through opening 115 of the metal cage and through opening 125 of the insert. Referring to FIG. 4A-FIG. 4D, metal cage 112 has a slot opening 114 in the front side 112a, slot opening 118 in the back side 112b, depressions 111 on the top and bottom surfaces, and through openings 117a, 117b starting in the back side 112b and extending diagonally toward the bottom and top surfaces 112f, 112e, respectively. Through openings 117a, 117b are dimensioned to receive the bone engaging fasteners 140a, 140b, respectively. Metal cage 112 also includes a through opening 116 having a rectangular perimeter and extending from the top surface 112e to the bottom surface 112f. There is also a pin receiving opening 115, as was mentioned above. Slot opening 114 is shaped and dimensioned to receive insert 120 which has a complementary shape and dimensions. Slot opening 118 is formed in the back side 112b and is shaped and dimensioned to receive the two planar pins 130a, 130b. The left and right inner sides of opening 118 include top and bottom upward and downward curved grooves 119b, 119d and 119a, 119c, respectively. The left and right inner sides of opening 118 also include central grooves 119e, 119f and openings 119g, 119h, respectively. Planar pins 130a, 130b are curved downwards and upwards, respectively, and their sides are dimensioned to slide within grooves 119a, 119c, and 119b, 119d, respectively. The top and bottom surfaces 112e, 112f of the metal cage 112 have bone engaging teeth 113. Planar pin 130a is made of metal and includes a downward curved body 132a having a rectangular central through opening 133a and a central pin 138a. Central pin 138a extends from the front surface of the planar pin 130a within the central opening 133a and has a distal end that projects in a direction opposite to the curvature of the planar pin 130a and engages the protrusion 111 in the bottom surface of the metal cage 112, when the metal planar pin 130a is in the "engaged position". The front end 134a is trapezoid shaped with the shortest side being in the front. The side surfaces 135a, 135b are partially smooth in order to facilitate sliding within grooves 119a, 119c. The front portion of side surfaces 135a, 135b includes teeth 136. The edges of the top surface also include teeth 137. Similarly, planar pin 130b is made of metal and includes an upward curved body 132b having a rectangular central through opening 133b and a central pin 138b extending from the front surface within the central opening 133b. Central pin 138b extends from the front surface within the central opening 133b and has a distal end that projects in a direction opposite to the curvature of the planar pin 130b and engages the protrusion 111 in the top surface of the metal cage 112, when the metal planar pin 130b is in the "engaged position". The front end 134b is trapezoid shaped with the shortest side being in the front. The side surfaces 135a, 135b are partially smooth in order to facilitate sliding within grooves 119b, 119d. The front portion of side surfaces 135a, 135b includes teeth 136. The edges of the top surface also include teeth 137. In the "non-engaged" configuration pins 130a, 130b are parallel to each other and are stored within opening 118 of the metal cage 112, as shown in FIG. 1 and FIG. 5A. In the "engaged" configuration pin 130a is curved downward and pin 130b is curved upward, and their front ends 134a, 134b project out of the metal cage 112, as shown in FIG. 2 and FIG. 5B. The front ends 134a, 134b and the teethed front sides 135a, 135b engage the superior and inferior vertebral endplates, respectively.

In operation, interbody cage 110 including the metal cage 112, the insert 120 and planar pins 130a, 130b is inserted within an intervertebral opening between two adjacent vertebras. A special inserter 180 is used to insert the interbody cage 110 within the intervertebral opening. Next, the inserter 180 pushes the back of the top and bottom pins 130b, 130a, and moves them upward and downward, respectively. The top and bottom pins 130b, 130a slide forward within grooves 119b, 119d and 119a, 119c, respectively, and engage the top vertebral endplate and the bottom vertebral endplate with their front ends 134b, 134a, and teethed front side surfaces 136b, 136a, respectively. Next, the two bone fasteners 140a, 140b are inserted into the interbody cage openings 117a, 117b, respectively, and they are screwed into the vertebral bodies. Bone fastener 140a is directed diagonally toward the bottom surface of the interbody cage 112 and engages the adjacent bottom vertebral body. Bone fastener 140b is directed diagonally toward the top surface of the interbody cage 112 and engages the adjacent top vertebral body. In summary, the interbody cage 110 is secured in the intervertebral opening with the two bone engaging fasteners 140a, 140b and with the two metal planar pins 130a, 130b. A special removal tool 190 is used to disengage the planar pins 130b, 130a from the vertebral endplates, as will be described below.

Figure 6:
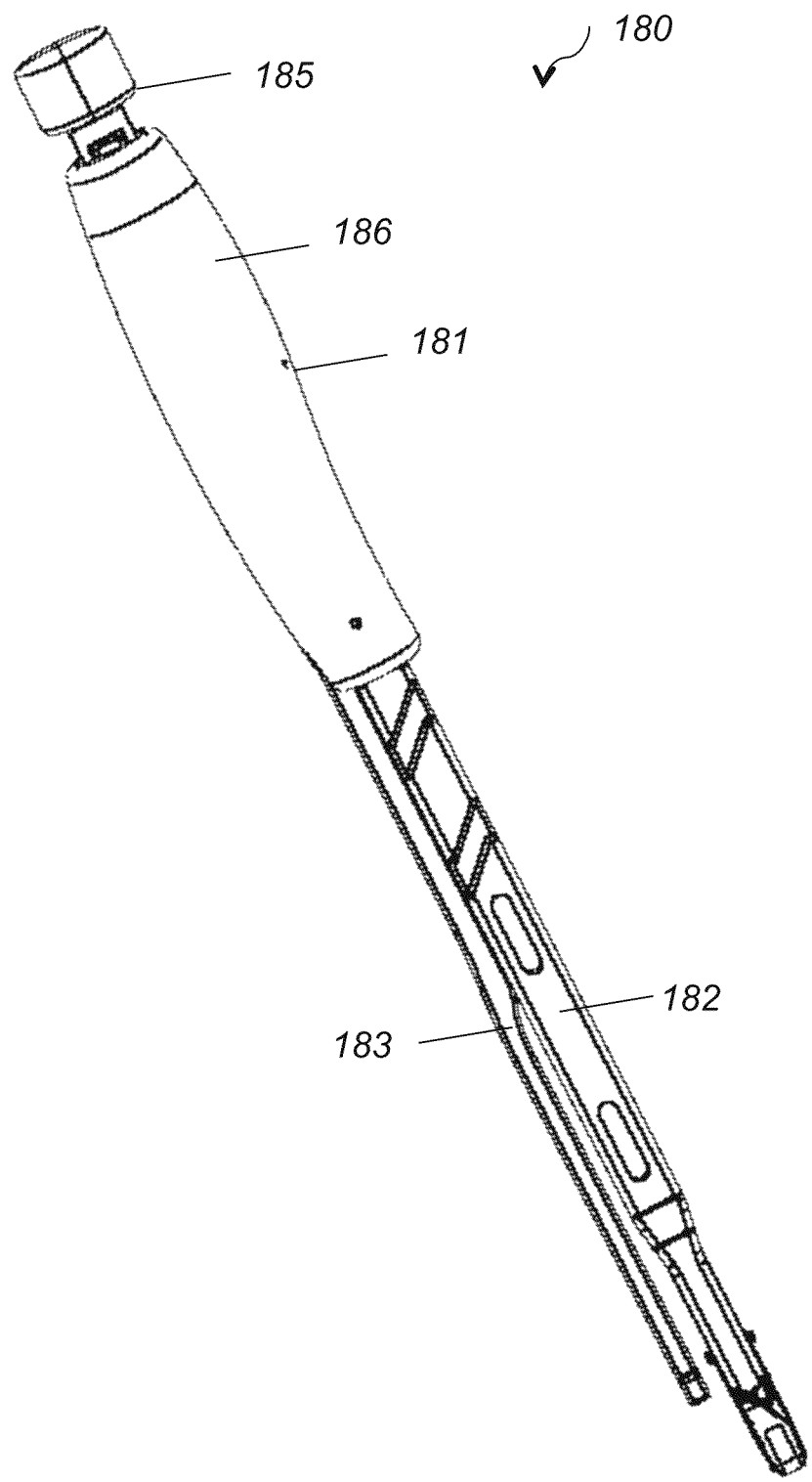
FIG. 6 is a perspective view of an inserter tool for the interbody cage of FIG. 3.
Figure 7A:
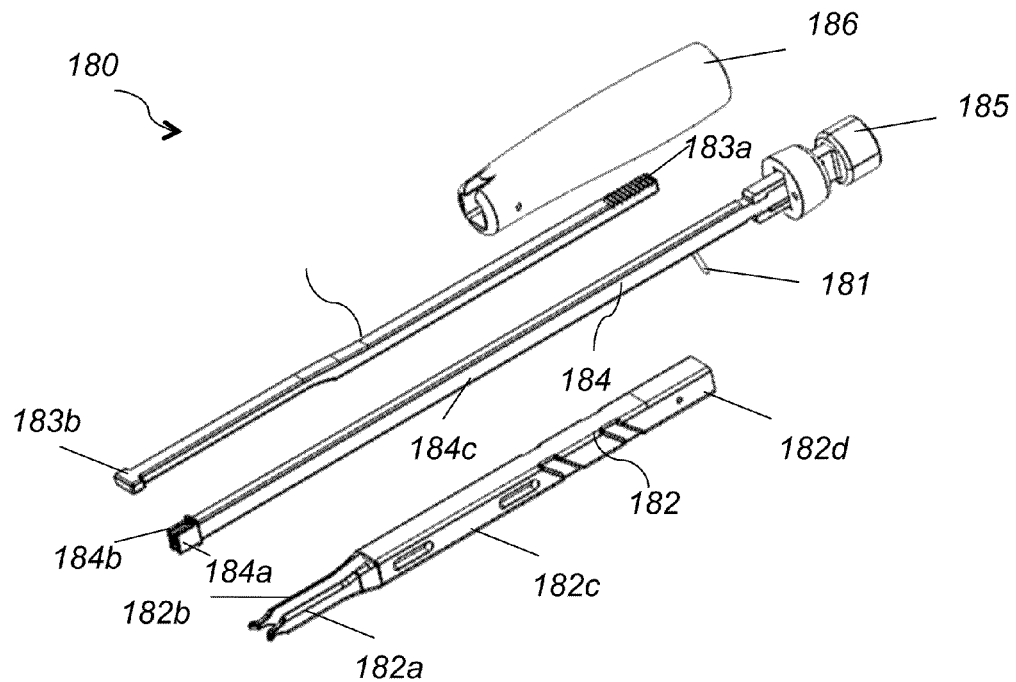
FIG. 7A is an exploded view of the inserter tool of FIG. 6.
Figure 7B:
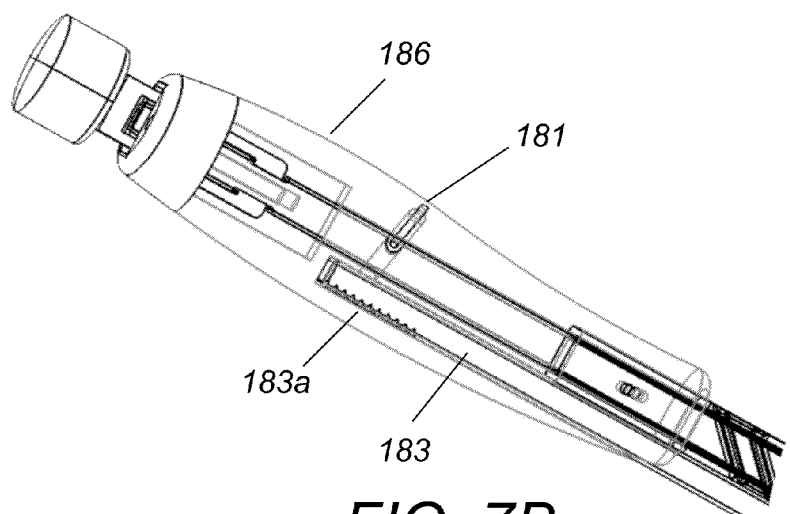
FIG. 7B is a transparent view of the handle of the inserter tool of FIG. 6.
Figure 8A:
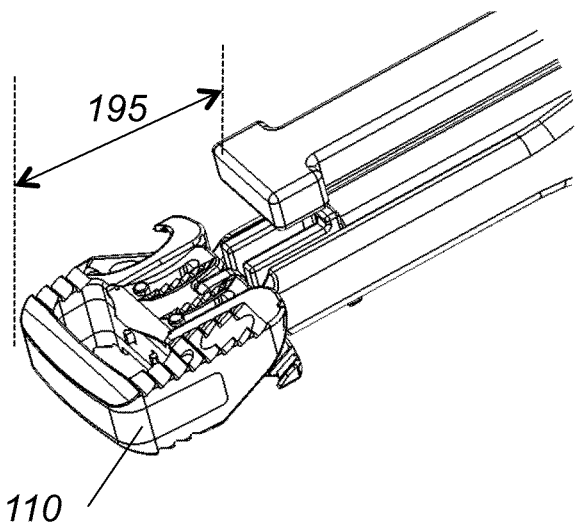
FIG. 8A is a detailed view of the distal portion of the inserter tool of FIG. 6 holding the interbody cage of FIG. 3.
Figure 8B:
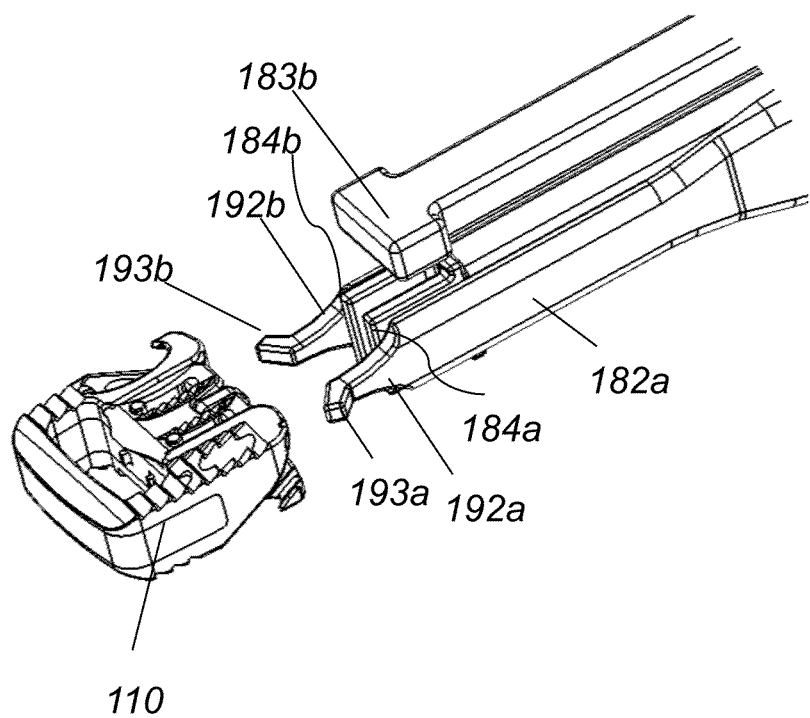
FIG. 8B is a detailed view of the distal portion of the inserter tool of FIG. 6.
Figure 9A:
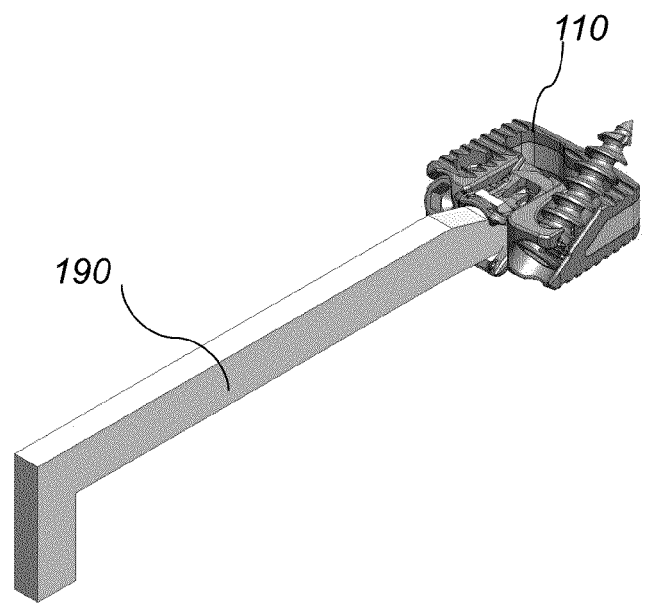
FIG. 9A is a perspective view of a pin removal tool having a distal end engaged with the interbody cage of FIG. 3.
Figure 9B:
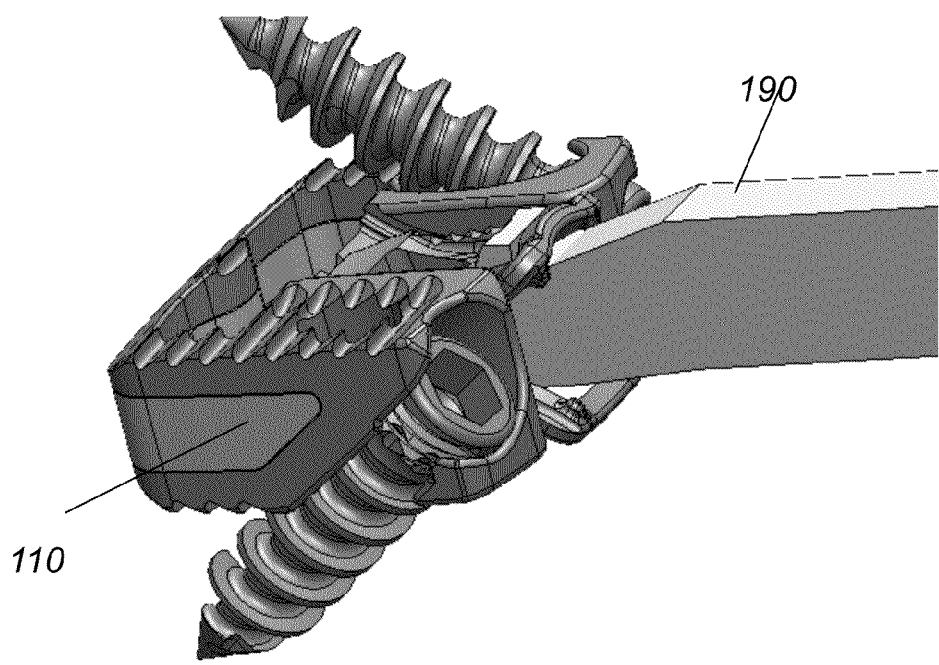
FIG. 9B is a detailed view of the distal end of the pin removal tool of FIG. 9A.
Figure 10A:
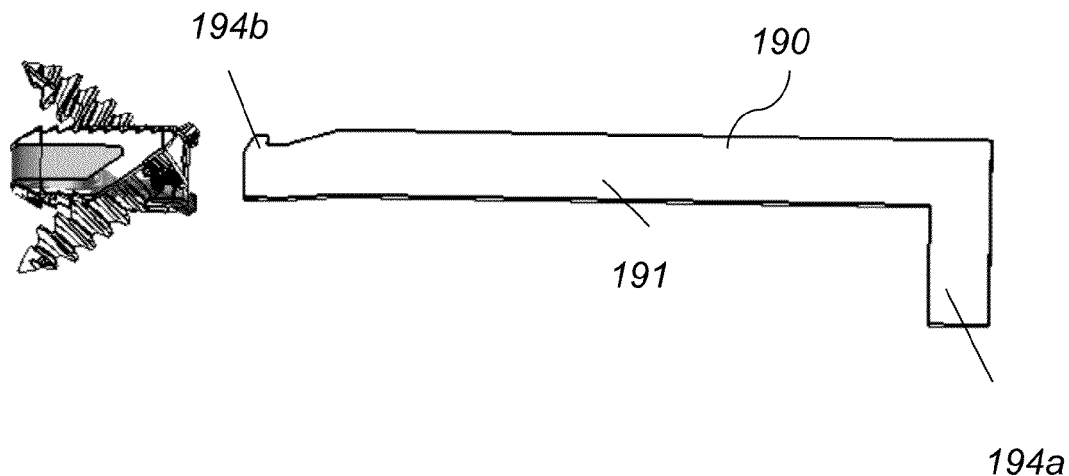
FIG. 10A is a side view of the pin removal tool.
Figure 10B:
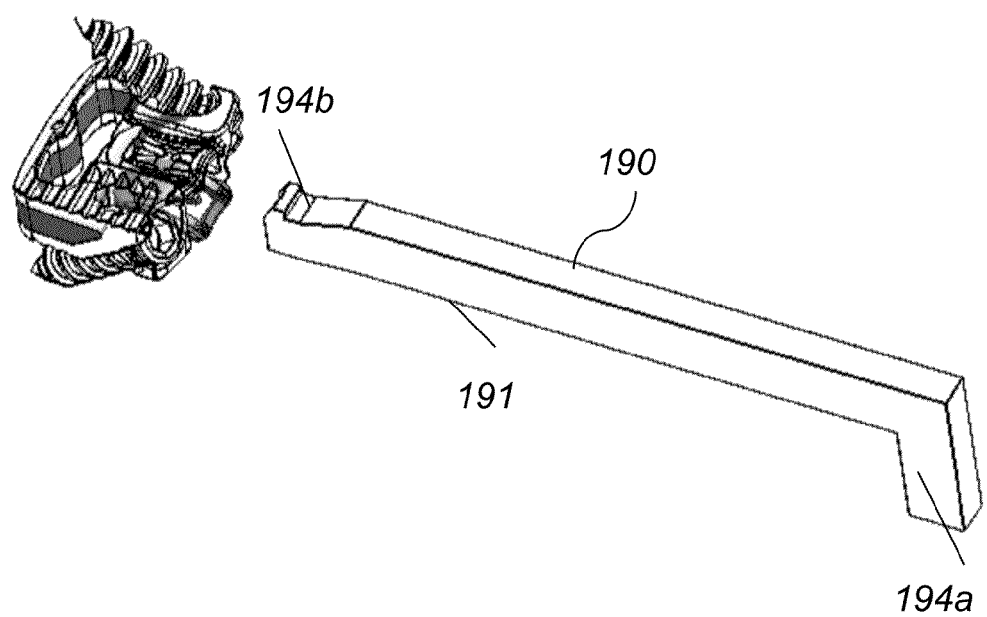
FIG. 10B is a top perspective view of the pin removal tool of FIG. 10A.

Referring to FIG. 6, inserter tool 180 includes a cannula 182, an impactor 184, a stop shaft 183, and a handle 186. Cannula 182 has an elongated body 182c with a central bore opening 182d and a rectangular cross section and terminates in two parallel distal extensions 182a, 182b extending from the distal end of the elongated body 182c. Impactor 184 slides within the cannula bore opening 182d slides impactor 184. Handle 186 surrounds the proximal end of the cannula 182 and is secured to it with a pin 181. Impactor 184 includes an elongated body 184c terminating in two parallel blades 184a, 184b. An impactor cap 185 is attached to the proximal end of the impactor elongated body 184c. Impactor cap 185 is used to push the impactor 184 forward. The cross section of the impactor's elongated body 184c matches the cross section of the cannula bore opening 182d and the two parallel blades 184a, 186b are oriented parallel to the distal extensions 182a, 182b of the cannula 182. Distal extensions 182a, 182b include trapezoid shaped ends 192a, 192b terminating in outward pointing tips 193a, 193b, respectively. Cannula 182 attaches to insert 100 by sliding distal extensions 182a, 182b into central grooves 119e, 119f of the insert 100 and inserting tips 193a, 193b into openings 119g, 119h, respectively. Once cannula 182 is attached to insert 100, the inserter 180 is used to guide and place the insert 100 in the prepared intervertebral opening between two adjacent vertebras. After placing the insert 100 in the intervertebral opening, the impactor cap 185 is pushed forward to move blades 184a, 184b forward and thereby to push planar pins 130a, 130b downward and upward within grooves 119a, 119c and 119b, 119d, respectively. Stop shaft 183 is oriented parallel to the cannula 182 and impactor 184 and includes ratchet grooves 183a at the proximal end and a curved front end 183b at the distal end. The position of the stop shaft 183 is adjusted via the ratchet grooves and is set at a fixed distance 195 from the intervertebral opening. Stop shaft 183 prevents overextending the cannula 182 past the set fixed distance 195. Pins 130a, 130b are moved in the "non-engaged" position by inserting a removal tool 190 into openings 133a, 133b, respectively. Removal tool 190 includes an elongated shaft 192 having a handle 192a at the proximal end a hook 192b at the distal end, as shown in FIG. 9A, FIG. 9B, FIG. 10A, FIG. 10B. Hook 192b is shaped and dimensioned to fit within openings 133a, 133b of planar pins 130a, 130b, respectively, and thereby attaches the hook tool to the planar pins. Once the hook tool 190 is attached to the planar pins 130a, 130b, it is pull back to move the planar pins 130a, 130b back into the "non engaged position", as shown in FIG. 9B.

Figure 11A:
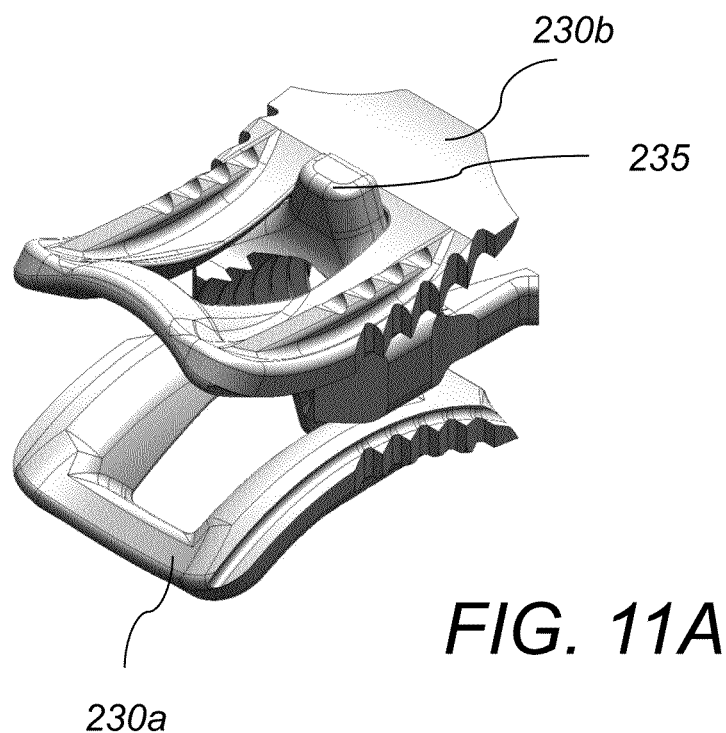
FIG. 11A is another embodiment of the planar pins in the 'non-engaged" position.
Figure 11B:
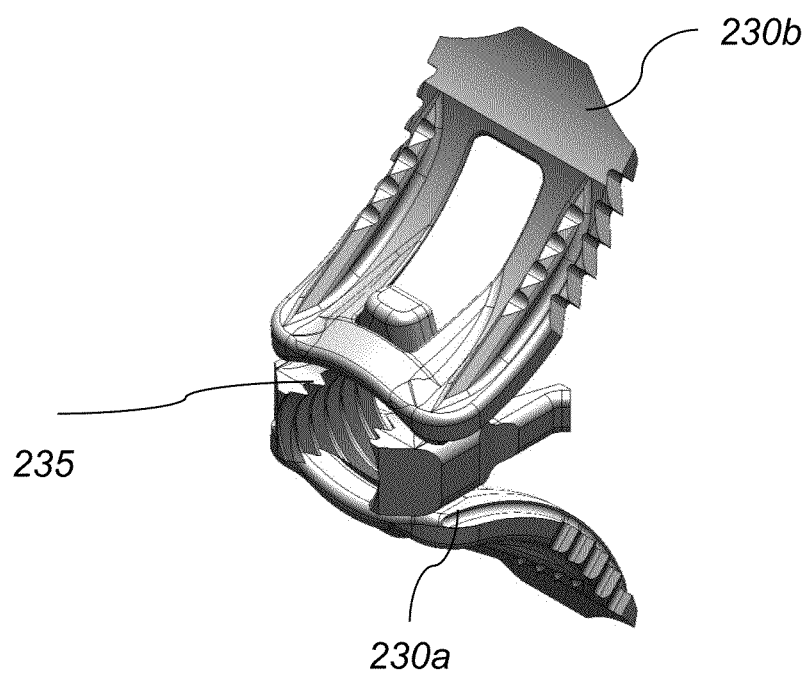
FIG. 11B depicts the planar pins of FIG. 11A in the 'engaged" position.
Figure 12:
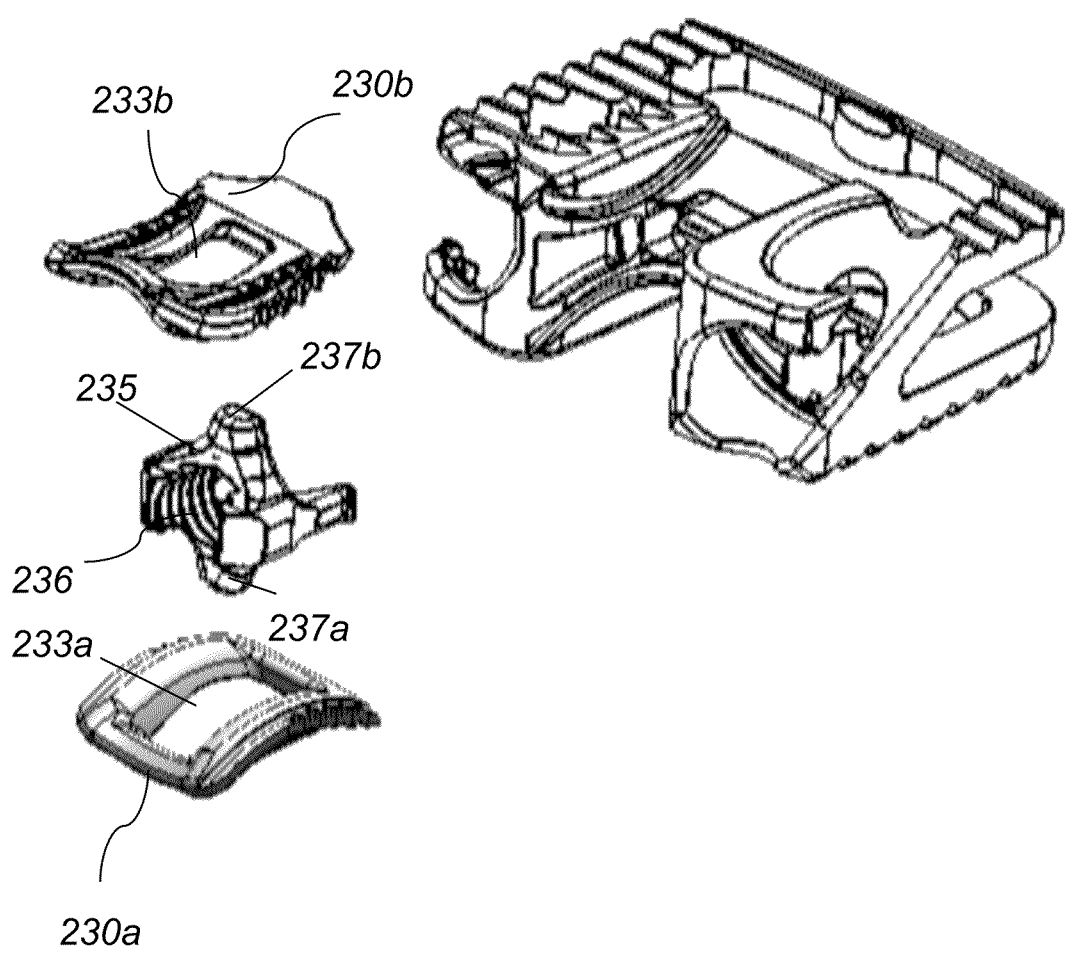
FIG. 12 is an exploded view of the planar pins of FIG. 11A.
Figure 13A:
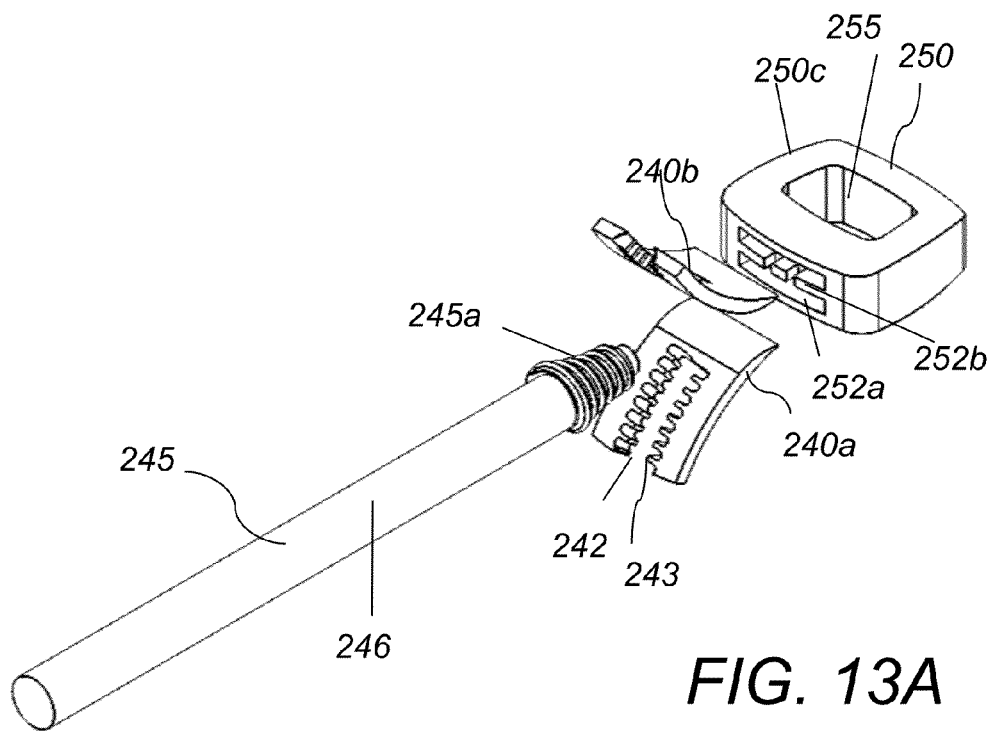
FIG. 13A depicts another embodiment of the interbody spinal fusion assembly and inserted tool, according to this invention.
Figure 13B:
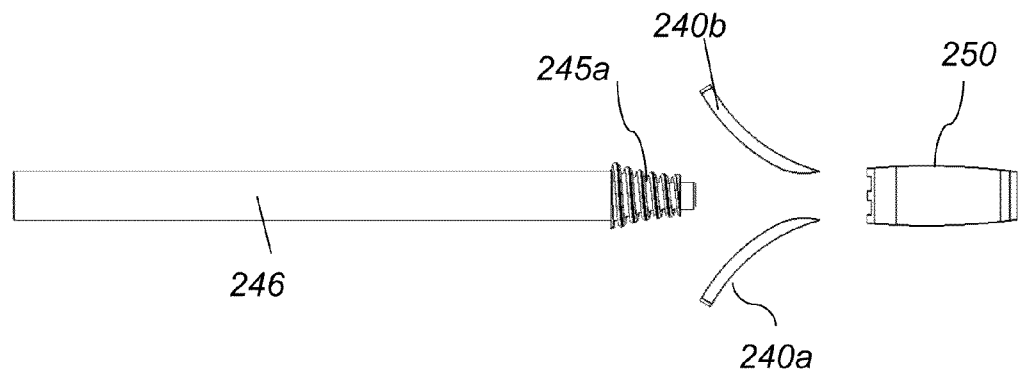
FIG. 13B is a side view of the interbody spinal fusion assembly and inserted tool of FIG. 13A.
Figure 13C:
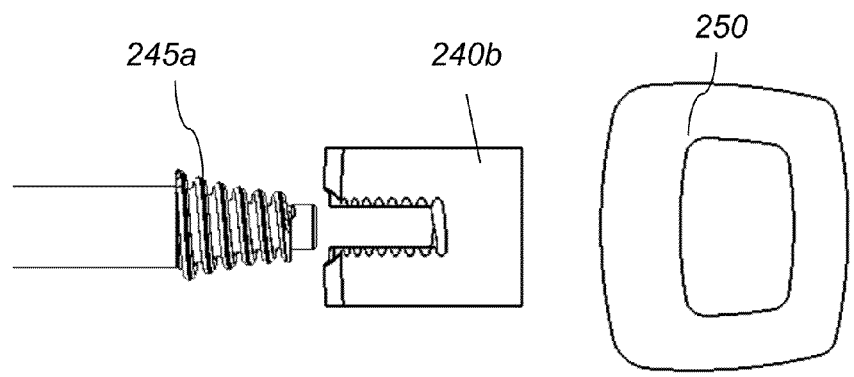
FIG. 13C is a top view of the interbody spinal fusion assembly and inserter tool of FIG. 13A.
Figure 14A:
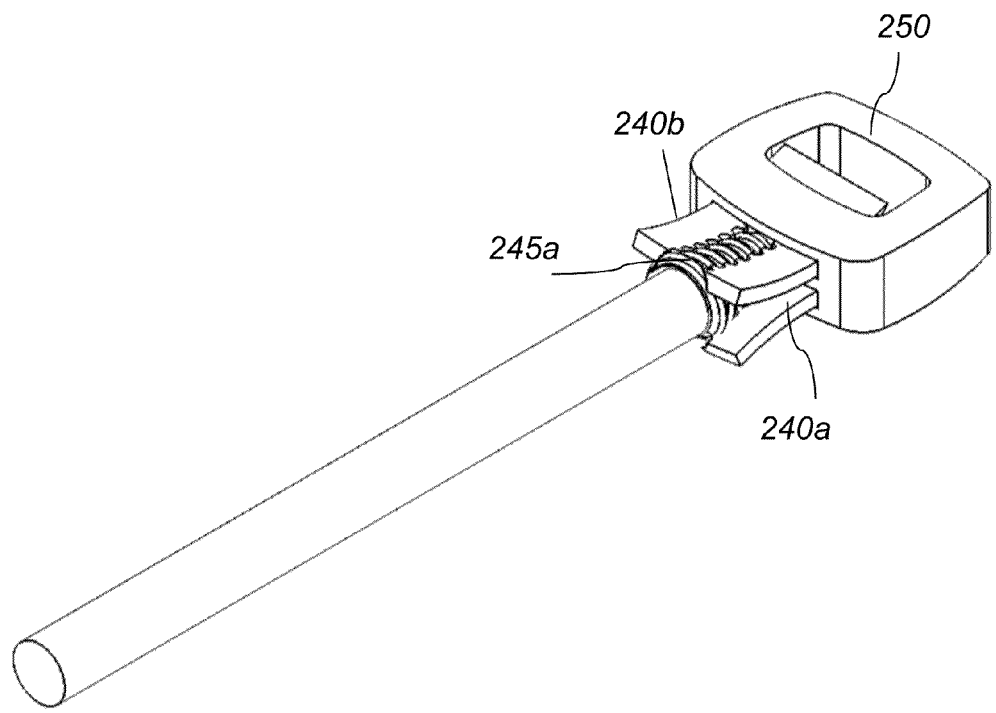
FIG. 14A is perspective view of the interbody spinal fusion assembly of FIG. 13A engaged with the inserter tool of FIG. 13A.
Figure 14B:
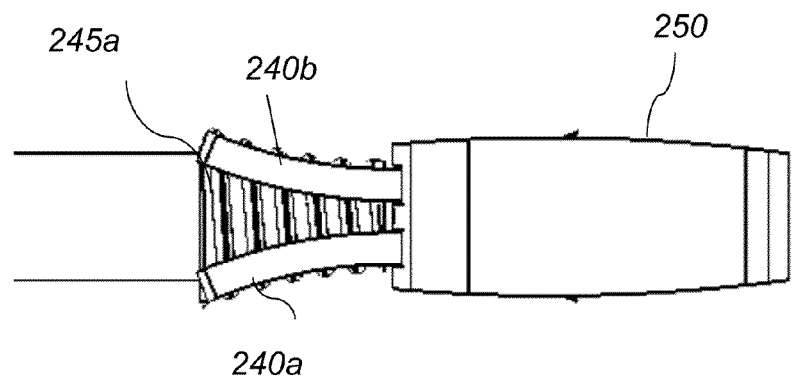
FIG. 14B is a side view of the distal end of the interbody spinal fusion assembly engaged with the inserter tool of FIG. 13A.
Figure 15A:
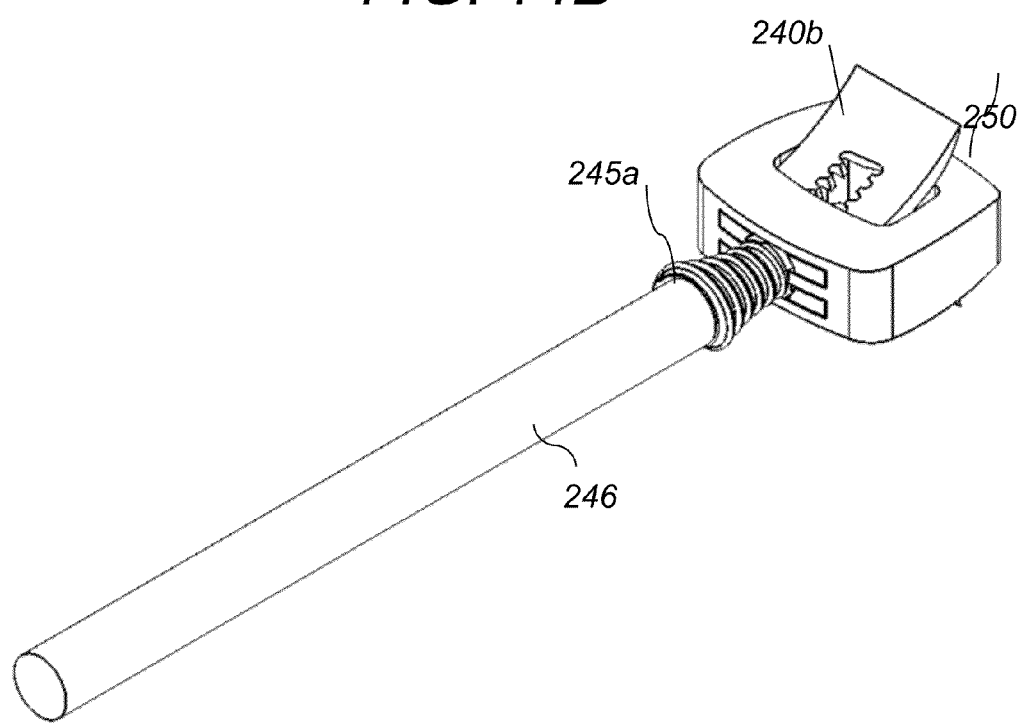
FIG. 15A is perspective view of the interbody spinal fusion assembly of FIG. 13A engaged with the inserter tool of FIG. 13A with the planar pins in the "engaged position"
Figure 15B:
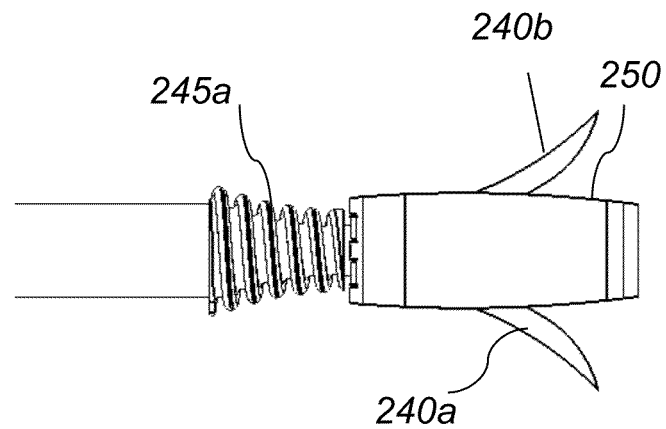
FIG. 15B depicts a side view of assembly of FIG. 15A.
Figure 15C:
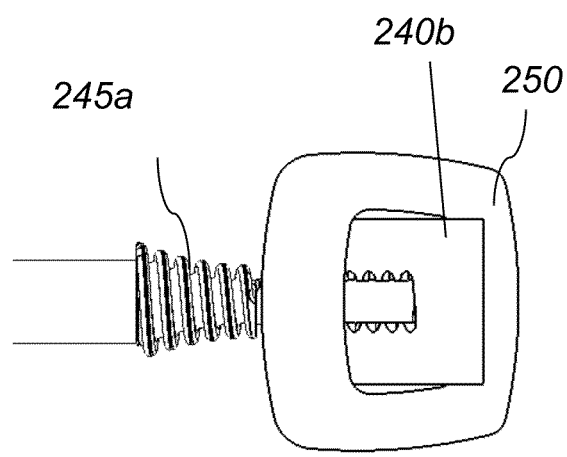
FIG. 15C depicts a top view of the assembly of FIG. 15A.
Figure 16A:
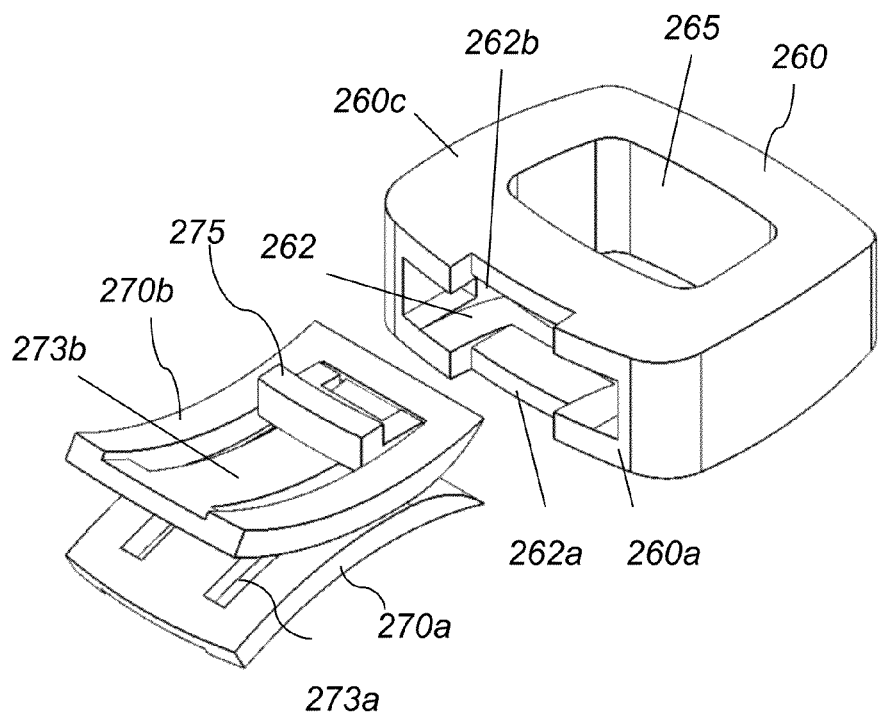
FIG. 16A depicts another embodiment of the interbody spinal fusion assembly, according to this invention.
Figure 16B:
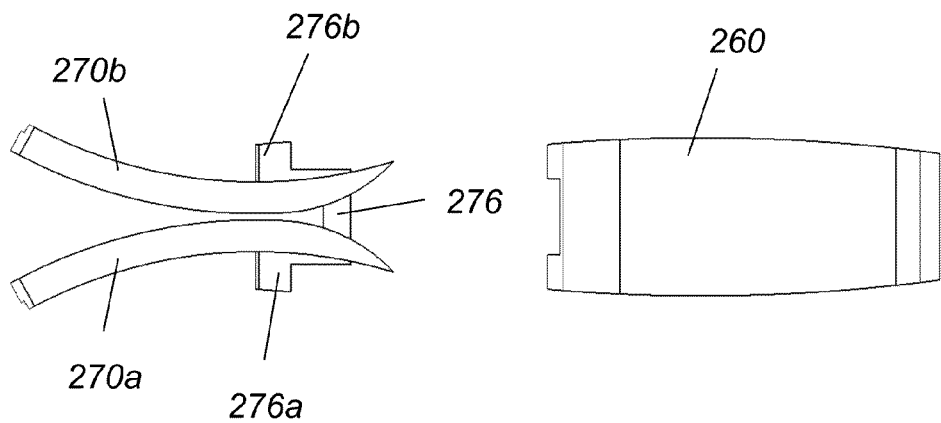
FIG. 16B depicts a side view of the interbody spinal fusion assembly of FIG. 16A.
Figure 16C:
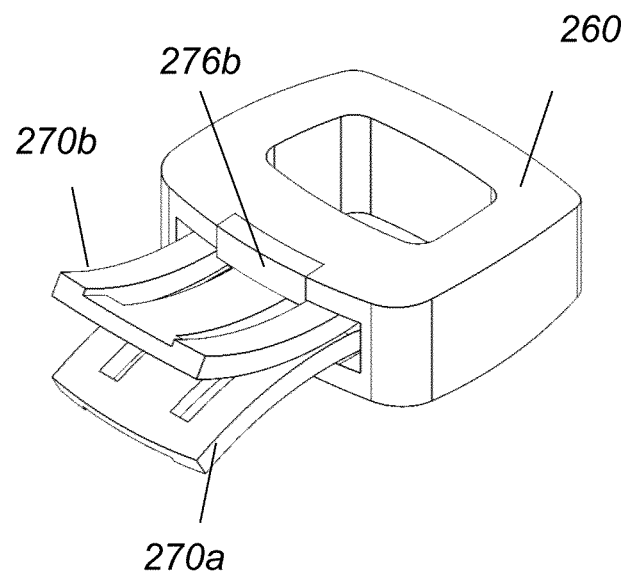
FIG. 16C depicts the embodiment of the interbody spinal fusion assembly of FIG. 16A with the planar pins partially engaged.
Figure 16D:
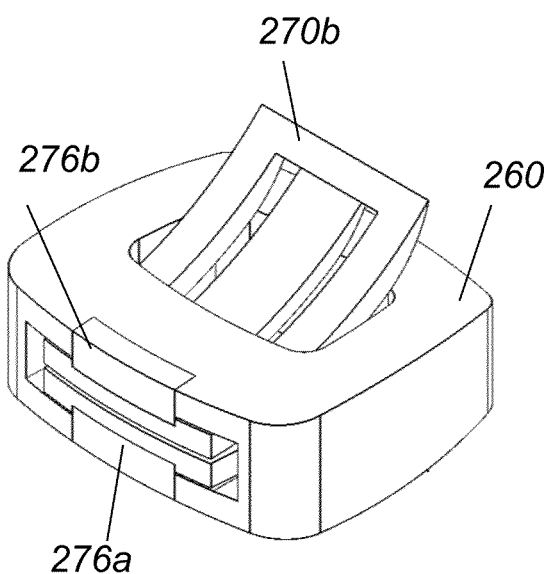
FIG. 16D depicts the embodiment of the interbody spinal fusion assembly of FIG. 16A with the planar pins fully engaged.
Figure 17A:
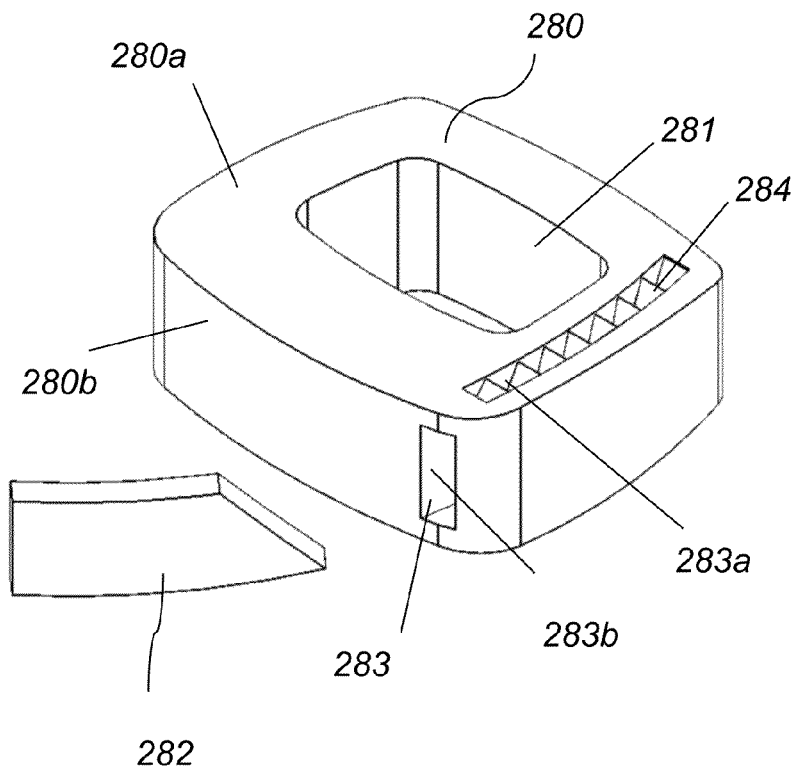
FIG. 17A depicts another embodiment of the interbody spinal fusion assembly, according to this invention.
Figure 17B:
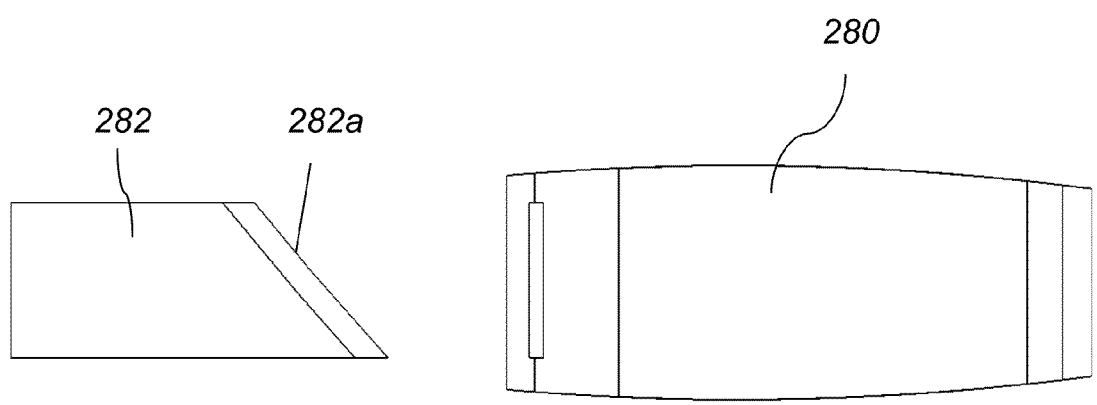
FIG. 17B depicts a side view of the interbody spinal fusion assembly of FIG. 17A.
Figure 17C:
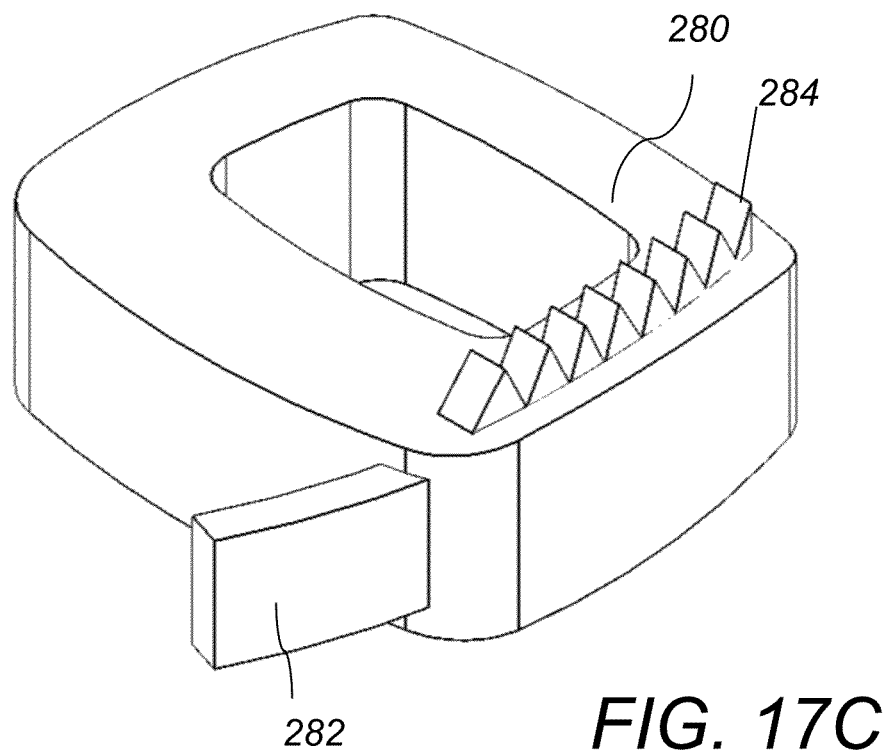
FIG. 17C depicts the embodiment of the interbody spinal fusion assembly of FIG. 17A with a planar pin partially engaged.
Figure 17D:
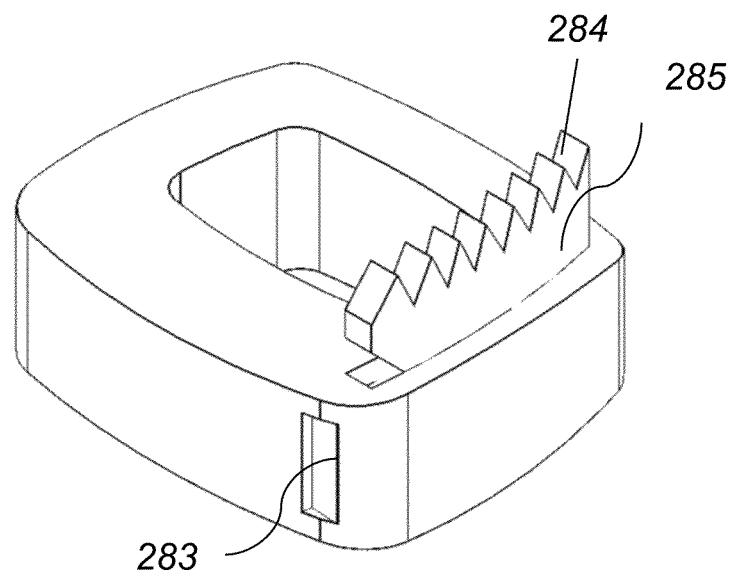
FIG. 17D depicts the embodiment of the interbody spinal fusion assembly of FIG. 17A with a planar pin fully engaged.
Figure 17E:
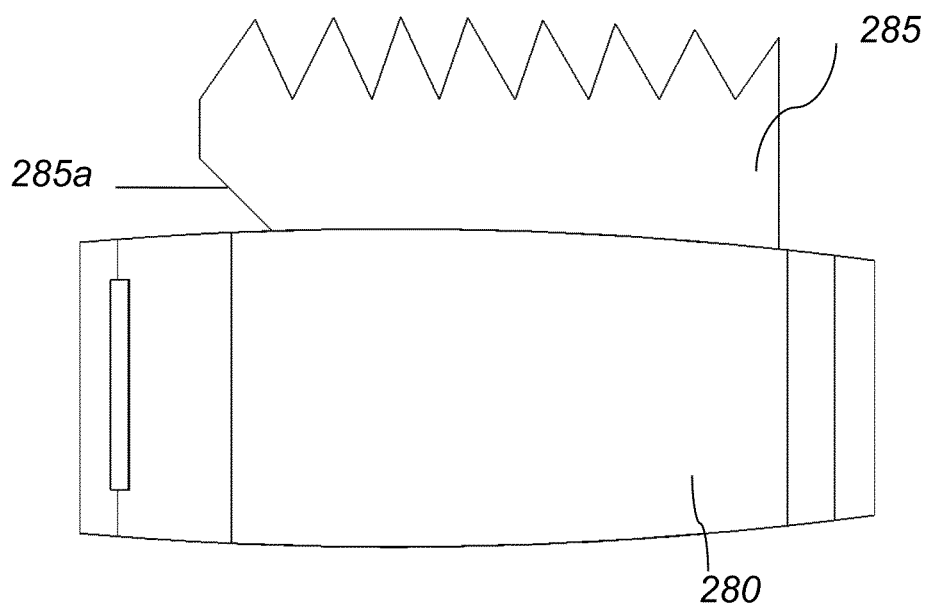
FIG. 17E depicts a side view of the embodiment of FIG. 17D.

In another embodiment, planar pins 230a, 230b include a center link member 235, as shown in FIG. 11A, FIG. 11B and FIG. 12. In this embodiment, each of the planar pins 230b, 230a, includes an upward or downward curved body 132a having a rectangular central through openings 233a. The front end 234a is trapezoid shaped with the shortest side being in the front. The side surfaces 235a, 235b are partially smooth in order to facilitate sliding within grooves 119a, 119c. The front portion of side surfaces 235a, 235b includes teeth 136. Center link member 235 slides between planar pins 230a, 230b and connects them. Center link member 235 includes a threaded through opening 236 and upward and downward extensions 237a, 237b. Extensions 237a, 237b are inserted into the central openings 233a of the planar pins and thereby engage the planar pins. An inserter tool (not shown) with a threaded distal end is inserted into the threaded opening 236 and is used to move the planar pins 230a, 230b simultaneously forward or backward into the "engaged" or "non-engaged" positions, respectively.

Referring to FIG. 13A, FIG. 13B, FIG. 13C, FIG. 14A, FIG. 14B and FIG. 15A-FIG. 15C, in another embodiment, the intervertebral cage 250 includes a body made of PEEK and has two slots 252a, 252b extending from the front 250a (proximal side) of the cage toward the center and a central through bore 255 extending from the top surface 250c to the bottom surface 250d of the cage 250. Two planar pins 240a, 240b with downward and upward curved bodies, respectively, are inserted into the slots 252a, 252b, with a helical inserter 245. Helical inserter 245 includes an elongated shaft 246 and a threaded conical distal end 245a. Each of the planar pins 240a, 240b includes a center slot 242 with inner teeth 243. As the helical inserter 245 is rotated, the threaded conical distal end 245a contacts the inner teeth 243 of the corresponding planar pins 240a, 240b and thereby engages them distally and moves them simultaneously forward into the corresponding slots 252a, 252b of the cage 250.

Referring to FIG. 16A, FIG. 16B, FIG. 16C, FIG. 16D, in another embodiment, the intervertebral cage 260 includes a body made of PEEK and has a slot 262, extending from the front 260a (proximal side) of the cage toward the center and a central through bore 265 extending from the top surface 260c to the bottom surface 260d of the cage 260. Two planar pins 270a, 270b with downward and upward curved bodies, respectively, are inserted into slots 262 with an inserter. Each of the planar pins 270a, 270b includes a rectangular opening 273a, 273b and they are connected to each other via a center link member 275 that slides within the openings 273a, 273b. Center link member 275 has a C-shaped body 276 and upward and downward extending extensions 276a, 276b, respectively. Extensions 276a, 276b fit within cutouts 262a, 262b formed in bottom and top surfaces 260d, 260c of the cage in the front 260a of the slot 262, and function as stops for the center link member 275 within the slot 262. The planar pins are held together with the center link member 275 and are inserted into the slot 262 simultaneously via impaction.

Referring to FIG. 17A, FIG. 17B, FIG. 17C, FIG. 17D, and 17E, in another embodiment, the intervertebral cage 280 includes a body made of PEEK and a vertical structure 285 recessed in a slot 283 having an opening 283a on the top surface 280a and an opening 283b in the front surface 280b. Vertical structure 285 has teeth 284 on the top surface and an inclined front surface 285a. A planar pin 282 is inserted into slot 283 through the front opening 283b. The front surface 282a of planar pin 282 is also inclined and it complements the inclined front surface 285a of vertical structure 285. Inserting of the pin 282 into slot 283 matches the two inclined surfaces 282a and 285a and raises the recessed vertical structure 285 up though the top opening 283a of the slot 283 and exposes the teeth 284. The exposed teeth 284 engage the vertebral endplate and secure the cage 280 in the intervertebral space. Intervertebral cage 280 also includes a central opening 281.

Figure 18A:
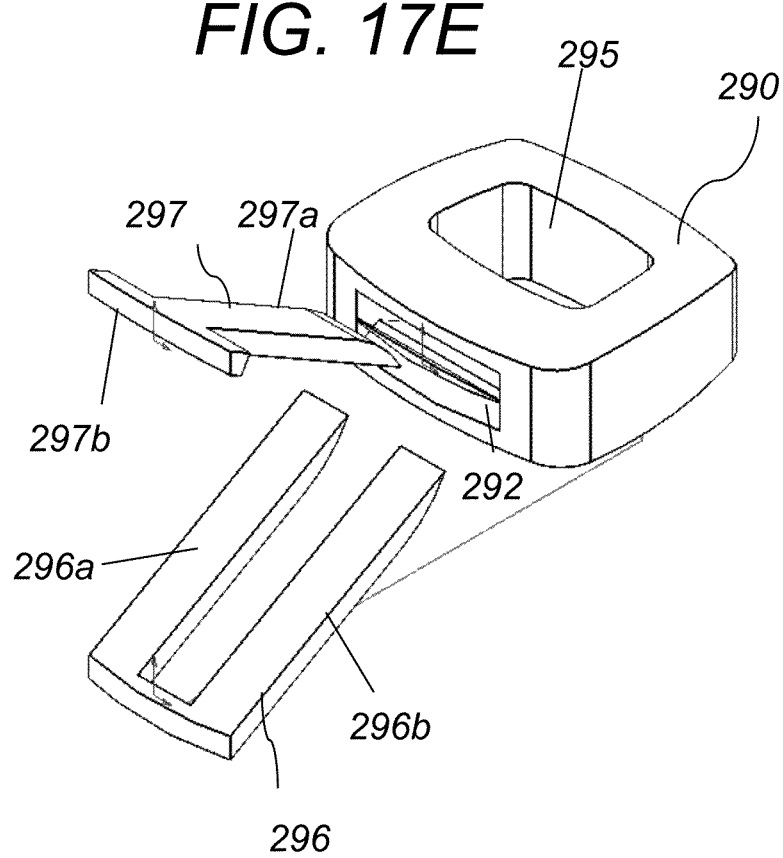
FIG. 18A depicts another embodiment of the interbody spinal fusion assembly, according to this invention.
Figure 18B:
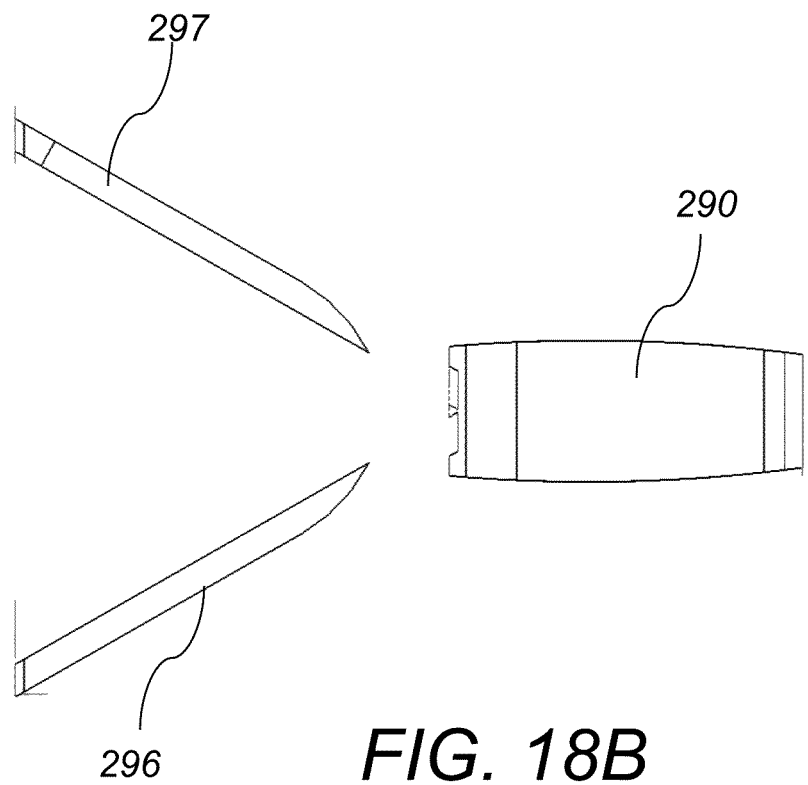
FIG. 18B depicts a side view of the interbody spinal fusion assembly of FIG. 18A.
Figure 18C:
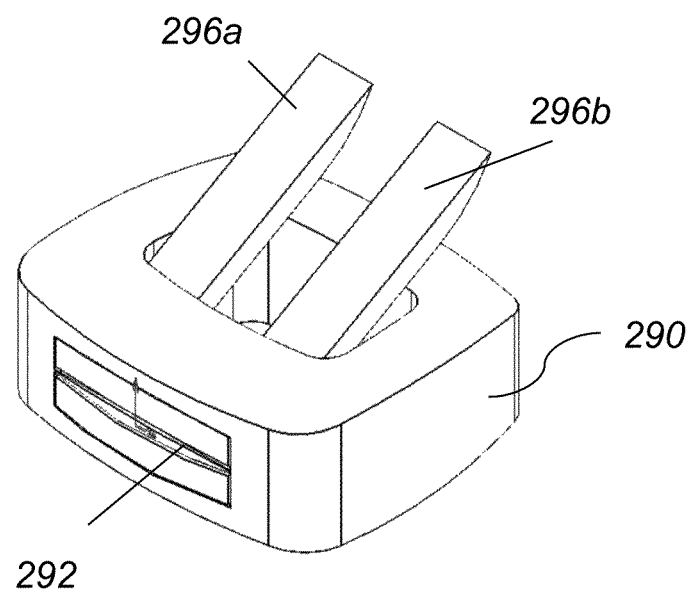
FIG. 18C depicts the embodiment of the interbody spinal fusion assembly of FIG. 18A with the flat pins fully engaged.
Figure 19A:
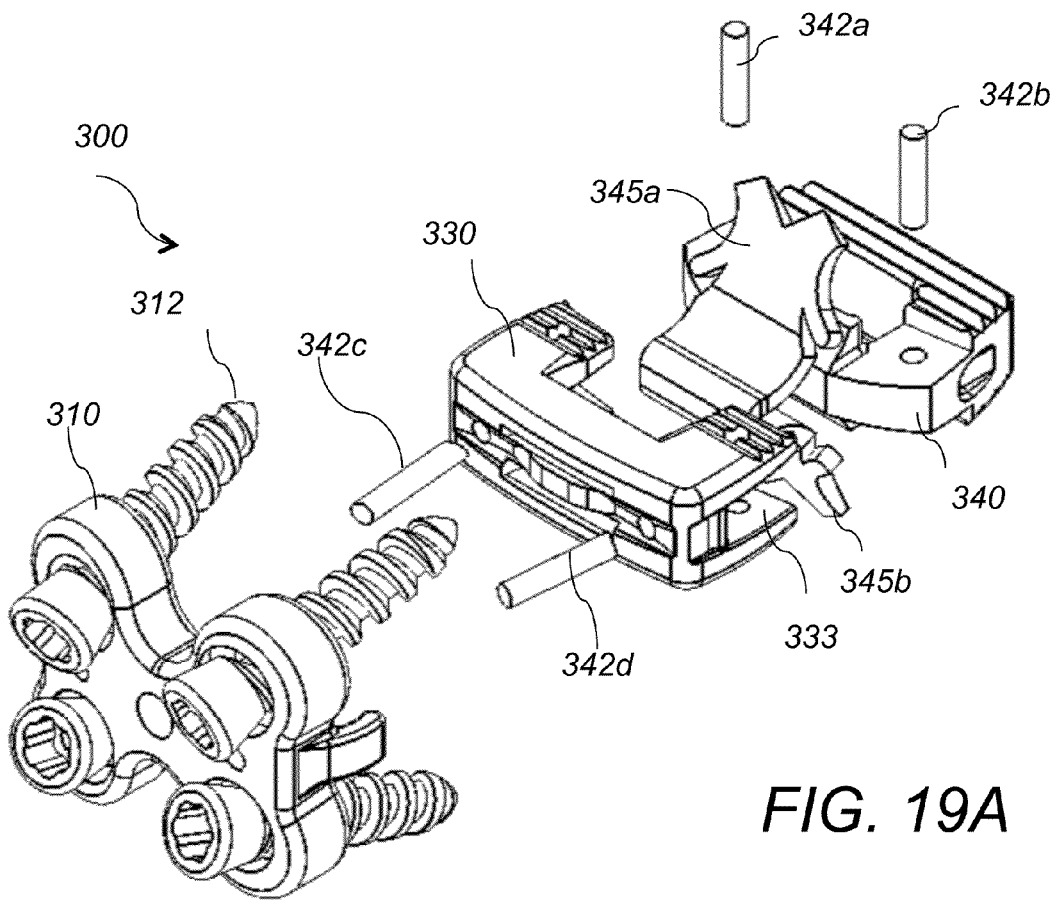
FIG. 19A depicts an exploded view of another embodiment of the interbody spinal fusion assembly, according to this invention.
Figure 19F:
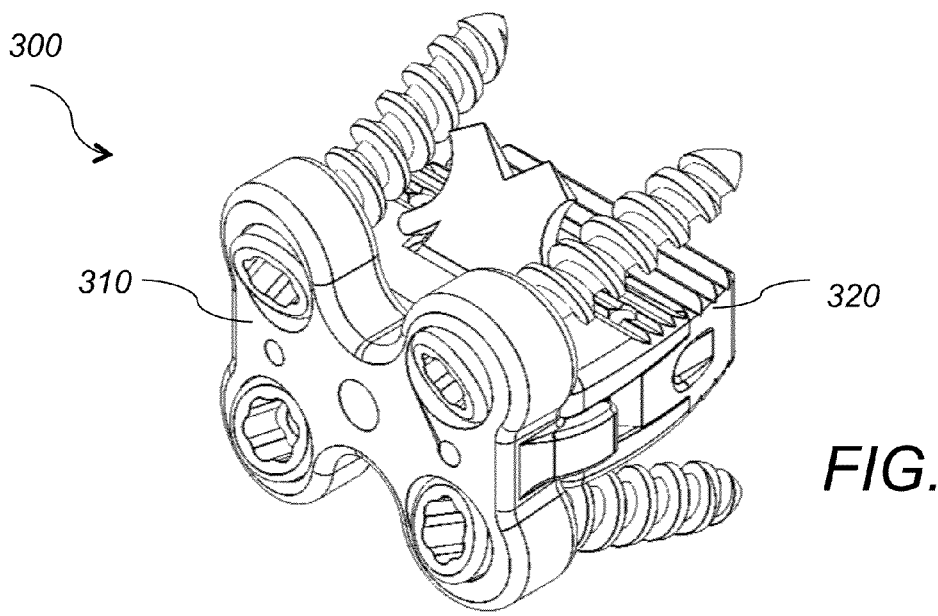
FIG. 19F depicts the assembled interbody spinal fusion assembly of FIG. 19A.
Figure 19B:
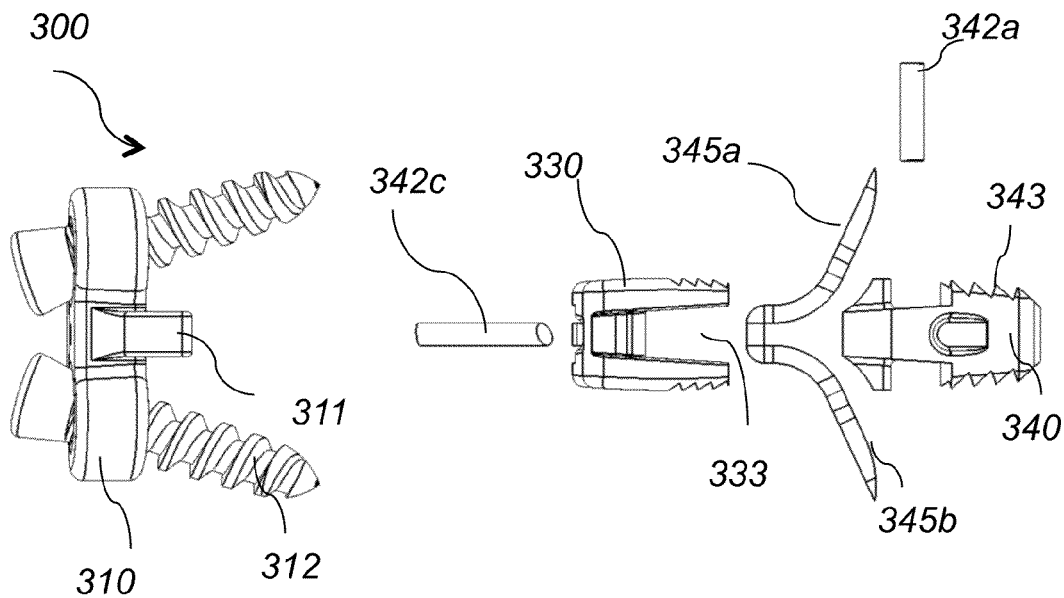
FIG. 19B depicts a side view of the interbody spinal fusion assembly of FIG. 19A.
Figure 19C:
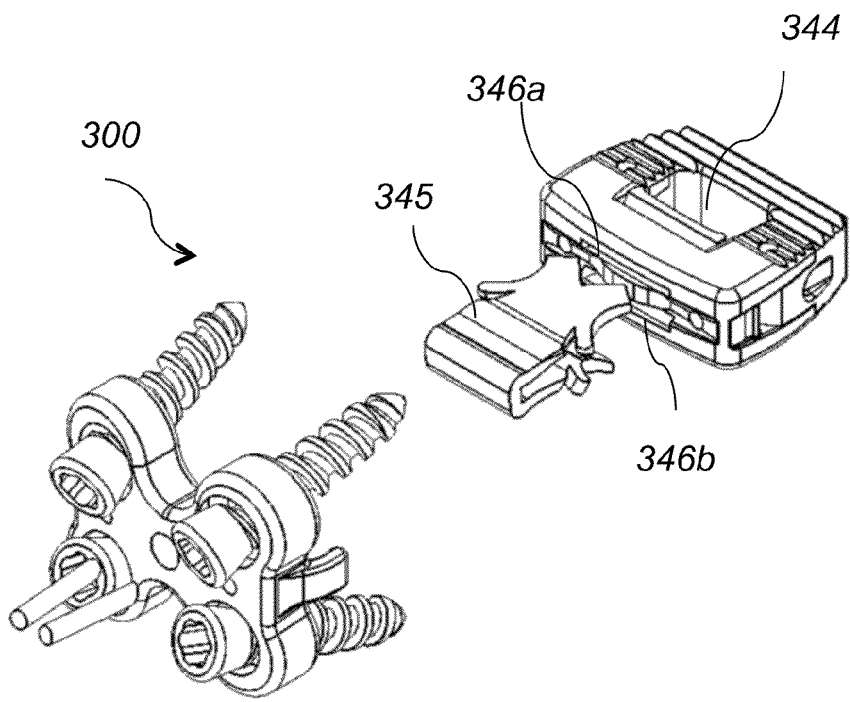
FIG. 19C depicts the first step in assembling the interbody spinal fusion assembly of FIG. 19A.
Figure 19D:
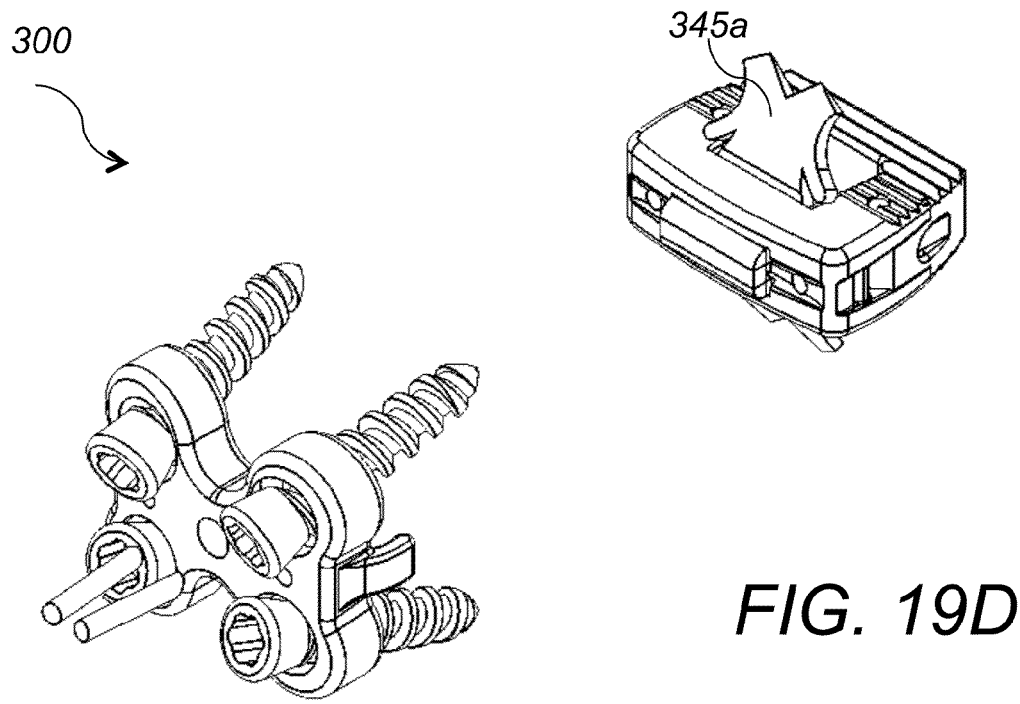
FIG. 19D depicts the embodiment of the interbody spinal fusion assembly of FIG. 19A with the planar pins fully engaged.
Figure 19E:
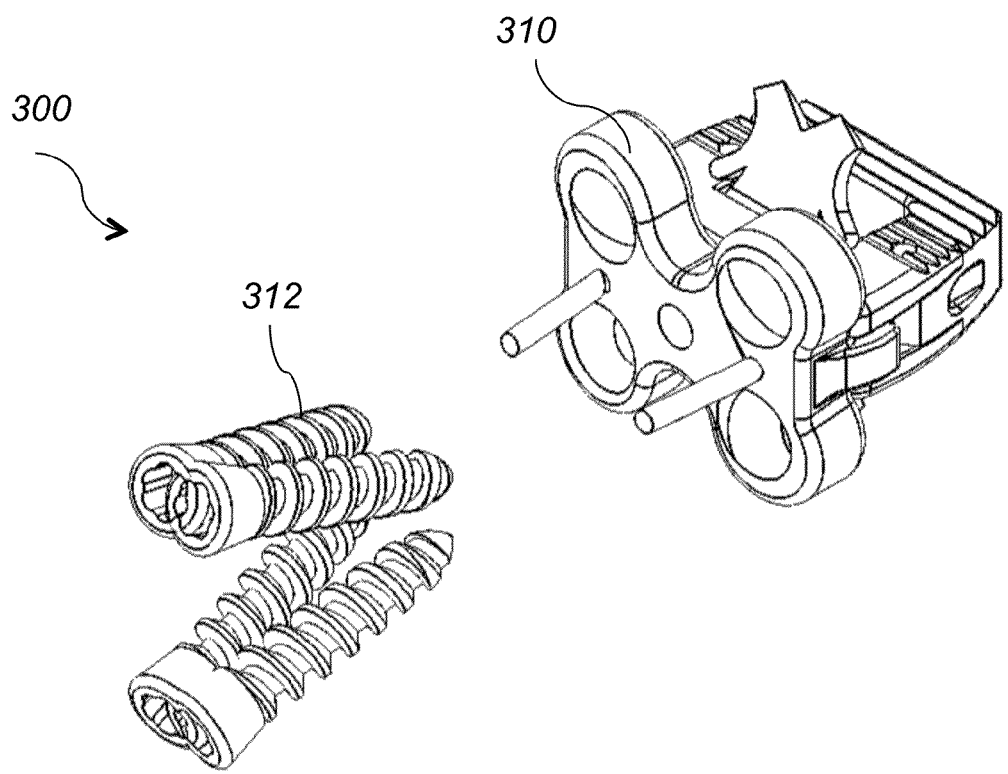
FIG. 19E depicts the second step in assembling the interbody spinal fusion assembly of FIG. 19A.

Referring to FIG. 18A, FIG. 18B, FIG. 18C, in another embodiment, the intervertebral cage 290 includes a body made of PEEK and has two intersecting front slots 292a, 292b, extending from the front 290a (proximal side) of the cage toward the center and a central through bore 295 extending from the top surface 290c to the bottom surface 290d of the cage 290. Two flat pins 296, 297 are inserted into slots 292a, 292b and they intersect each other as they pass through the central through bore 295. Flat pin 296 includes two rectangular shaped protrusions 296a, 296b connected at the proximal end by a cross bar 296c and separated by a rectangular opening 296b. Flat pin 297 includes a T shaped body having a rectangular shaped protrusion 297a and a cross-bar 297b attached to the proximal end of protrusion 297a. The distal ends of protrusions 296a, 296b, and 297a are pointed and engage the top and bottom vertebral endplates to secure the cage 290 in the intervertebral space.

Referring to FIG. 19A-FIG. 19F, in another embodiment, an intervertebral insert assembly 300 includes a two component cage body 320, two connected planar pins 345a, 345b and plate 310. Cage 320 includes a front component 330 made of PEEK and a back component 340 made of metal. The two components 330, 340 are held together with pins 342a, 342b, 331a, 332b and they form a rectangular shaped body having a central opening 344. The front surface of the front component 330 includes a slot 332, through which planar pins 345a, 345b are inserted. After inserting the assembled cage body 320 in the intervertebral space, the two connected planar pins 345a, 345b are compressed and are inserted into slot 332, When the planar pins 345a, 345b reach the central opening 344, they are released and their distal ends expand upward and downward, respectively, and they engage the top and bottom vertebral plates, respectively. Next, plate 310 is placed in front of the inserted cage 320 and vertebral bodies and is attached to the front surface of the cage 320 and the front surfaces of the vertebral bodies with four bone fasteners 312. Plate 310 includes four through opening dimensioned to receive the four bone fasteners 312.

Figure 20A:
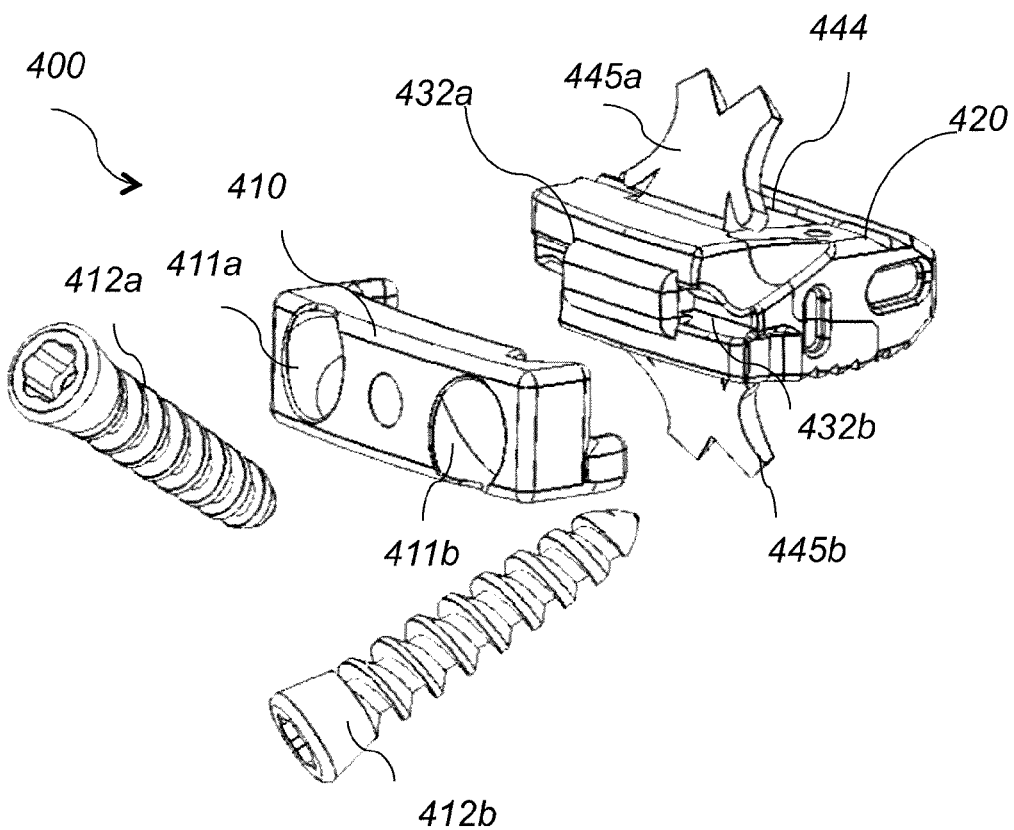
FIG. 20A depicts an exploded view of another embodiment of the interbody spinal fusion assembly, according to this invention.
Figure 20B:
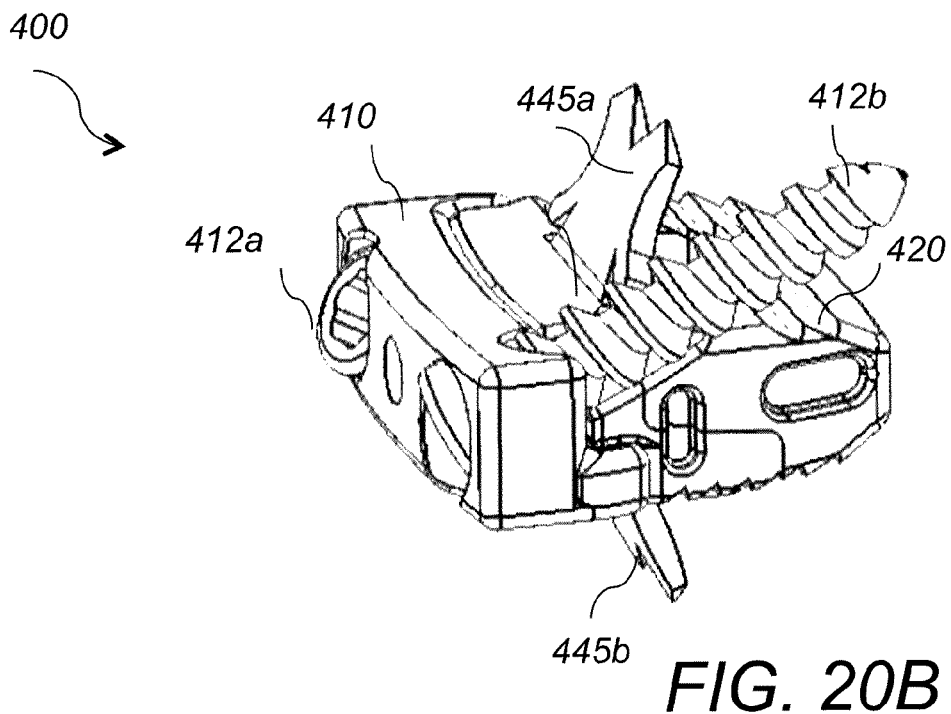
FIG. 20B depicts the assembled interbody spinal fusion assembly of FIG. 20A.

Referring to FIG. 20A and FIG. 20B, in another embodiment, the intervertebral insert assembly 400 includes a cage body 420, two planar pins 445a, 445b and plate 410. In this embodiment, plate 410 includes two openings 411a, 411b dimensioned to received bone fasteners 412a, 412b. After inserting the cage body 420 in the intervertebral space, the connected planar pins 445a, 445b are compressed and are inserted into slots 432a, 432b of body 420. When the planar pins 445a, 445b reach the central opening 444, they are released and their distal ends expand upward and downward, respectively, and they engage the top and bottom vertebral plates, respectively. Plate 410 is then attached to the front surface of the cage 420 with two bone fasteners 412a, 412b.

Figure 21A:
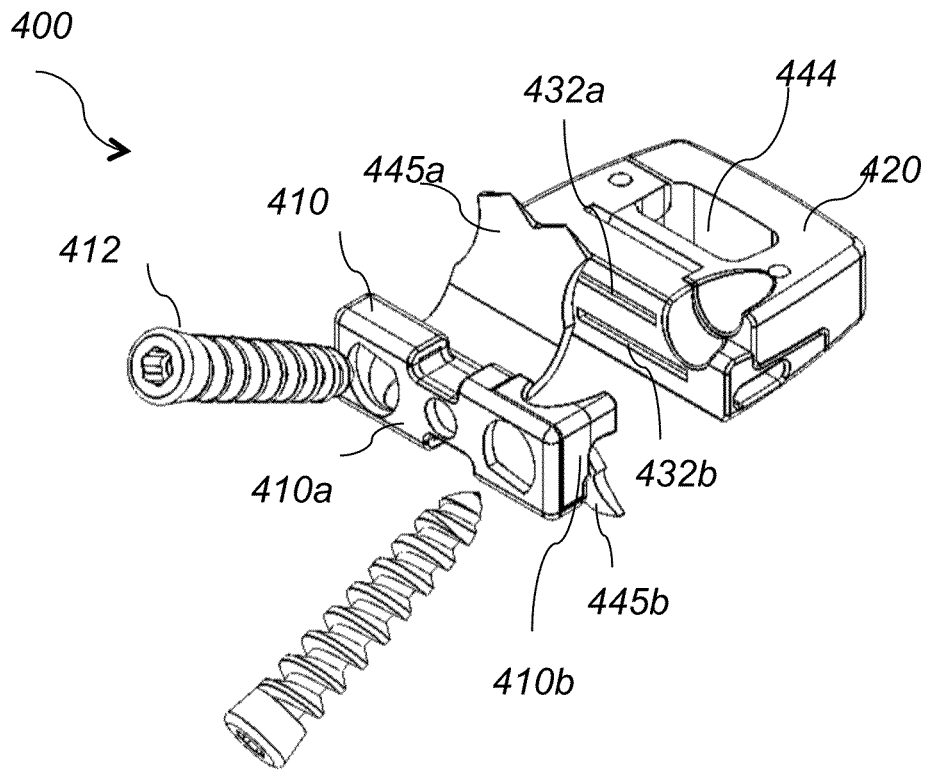
FIG. 21A depicts an exploded view of another embodiment of the interbody spinal fusion assembly, according to this invention.
Figure 21B:
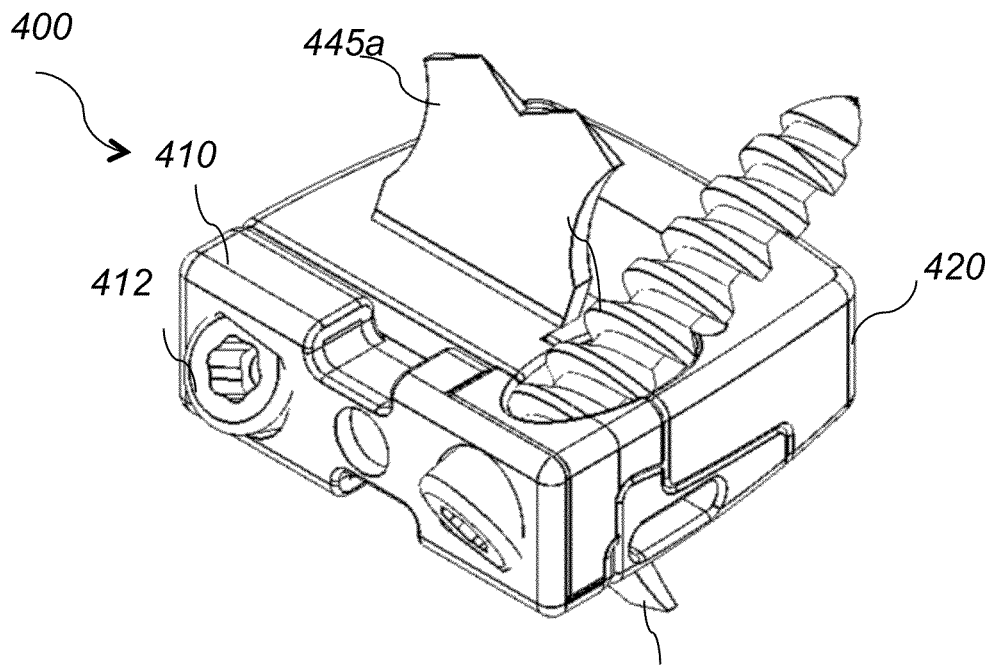
FIG. 21B depicts the assembled interbody spinal fusion assembly of FIG. 21A.
Figure 22A:
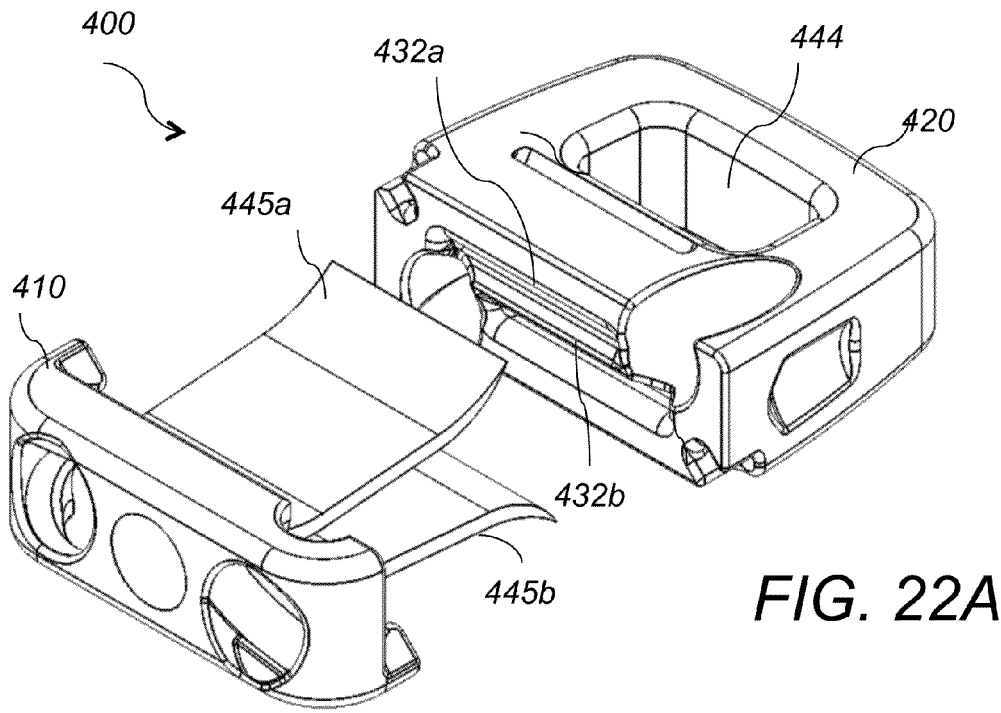
FIG. 22A depicts an exploded view of another embodiment of the interbody spinal fusion assembly, according to this invention.
Figure 22B:
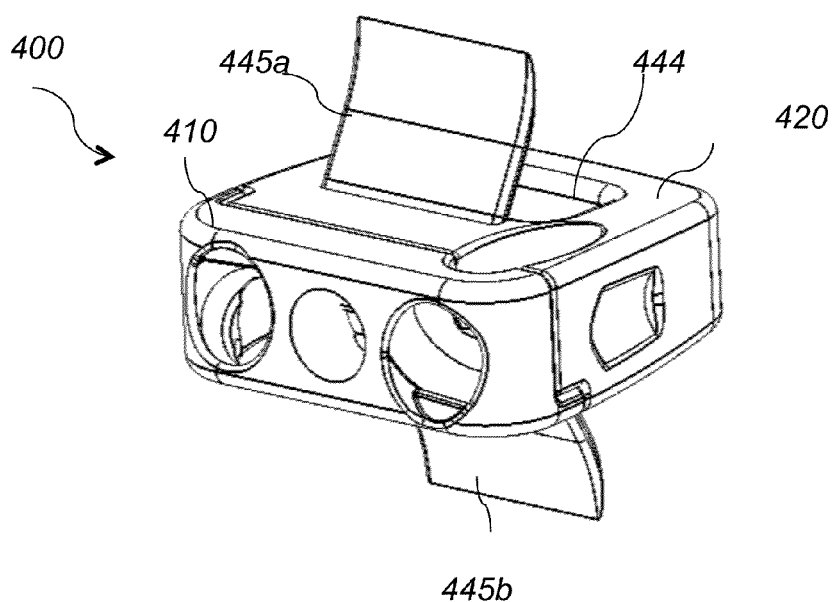
FIG. 22B depicts the assembled interbody spinal fusion assembly of FIG. 22A.

Referring to FIG. 21A and FIG. 21B, in another embodiment, the intervertebral insert assembly 400 includes a cage body 420, two planar pins 445a, 445b and plate 410. In this embodiment, plate 410 and planar pins 445a, 445b are connected and form one assembly. The main body of plate 410 is made of plastic 410b wrapped with a metal covering 410a. Pins 445a, 445b are made of metal and are part of the metal covering 410a of plate 410. After inserting the cage body 420 in the intervertebral space, the connected planar pins 445a, 445b are compressed and are inserted into slots 432a, 432b of body 420. When the planar pins 445a, 445b reach the central opening 444, they are released and their distal ends expand upward and downward, respectively, and they engage the top and bottom vertebral plates, respectively. Plate 410 is then attached to the front surface of the cage 420 with two bone fasteners 412a, 412b. In yet another embodiment, planar pins 445a, 445b are part of metal plate 410 and extend directly from plate 410, as shown in FIG. 22a and FIG. 22B.

Referring to FIG. 23A and FIG. 23B, in another embodiment, the intervertebral insert assembly 500 includes a cage body 520, and front component including a solid plate 510 and two planar pins 545a, 545b extending from and plate 410. The interbody cage 520 is made of PEEK and includes two front holes 522a, 522b configured to receive bone anchors 512a, 512b, and two recessed front slots 532a, 532b configured to receive planar pins 545a, 545b. The two recessed slot openings 532a, 532b are shaped and dimensioned to receive the compressed planar pins 545a, 545b. One of the two recessed slots is directed upward 532a and the other downward 532b. In this case, the interbody cage 520 is inserted into the intervertebral space and is secured with the anchors 512a, 512b. Next, the planar pins 545a, 545b are compressed and are inserted into slots 532a, 532b of body 520. When the planar pins 545a, 545b reach the central opening 544, they are released and their distal ends expand upward and downward, respectively, and they engage the top and bottom vertebral plates, respectively. Plate 510 is positioned in front of the bone anchors 512a, 512b and acts as an anti-backout feature for the bone anchors.

Several embodiments of the present invention have been described. Nevertheless, it will be understood that various modifications may be made without departing from the spirit and scope of the invention. Accordingly, other embodiments are within the scope of the following claims.

What is claimed is:

1. An interbody spinal fusion assembly configured for implantation at least partially between a superior vertebra and an inferior vertebra comprising:
    an interbody cage comprising left and right side surfaces, front and back surfaces and top and bottom surfaces;
    wherein the interbody cage comprises a metal cage, a plastic insert, and first and second planar metal pins;
    wherein the metal cage comprises a front slot extending from the front surface towards the center of the interbody cage and wherein the plastic insert is shaped and dimensioned to fit within the front slot;
    wherein the metal cage further comprises a back slot extending from the back surface towards the center of the interbody cage and wherein the first and second metal pins are shaped and dimensioned to fit and sit within the back slot; and
    wherein the front slot does not intersect with the back slot.

2. The interbody spinal fusion assembly of claim 1, wherein the back slot comprises left and right upwards curved grooves and left and right downwards curved grooves and wherein the first and second planar metal pins comprise left and right sides that are shaped and dimensioned to slide within the left and right upwards curved grooves and the left and right downwards curved grooves, respectively, after the implantation of the interbody cage, and wherein the left and right upwards curved grooves do not intersect with the left and right downwards curved grooves.

3. The interbody spinal fusion assembly of claim 1, further comprising first and second bone fasteners, and wherein the metal cage further comprises a top through opening extending from the top surface towards the bottom surface and first and second through openings starting in the back surface and extending diagonally towards the top and bottom surfaces, respectively, wherein the first and second through opening are dimensioned to receive the first and second bone fasteners, respectively.

4. The interbody spinal fusion assembly of claim 1, further comprising a pin and wherein the position of the plastic insert is secured within the front slot of the metal cage with the pin.

5. The interbody spinal fusion assembly of claim 1 wherein the top and bottom surfaces of the interbody cage comprise bone engaging teeth.

6. The interbody spinal fusion assembly of claim 1, wherein each of the first and second planar metal pins comprises an elongated curved body having a trapezoid shaped front end, a rectangular through opening and a central pin, and wherein the central pin extends from the front end of the elongated curved body within the rectangular opening and comprises a distal end projecting in a direction opposite to the curvature of the elongated curved body.

7. The interbody spinal fusion assembly of claim 6 wherein the metal cage further comprises top and bottom depressions on the top and bottom surfaces, respectively, and wherein the top and bottom depressions are shaped and dimensioned to engage the distal end of the central pin of the first and second planar metal pins, respectively.

8. The interbody spinal fusion assembly of claim 6, wherein the elongated curved body comprises a back portion with smooth left and right sides, a front portion with teethed left and right sides, and teeth along the left and right edges of the top surface.

9. The interbody spinal fusion assembly of claim 1, wherein the metal cage comprises one of titanium, stainless steel, biocompatible metal or alloys thereof.

10. The interbody spinal fusion assembly of claim 1, wherein the first and second planar metal pins comprise one of titanium, stainless steel, biocompatible metal or alloys thereof.

11. The interbody spinal fusion assembly of claim 1, wherein the plastic insert comprises PEEK.

12. A method for spinal stabilization comprising:
    providing an interbody spinal fusion assembly comprising an interbody cage, wherein the interbody cage comprises left and right side surfaces, front and back surfaces and top and bottom surfaces;
    wherein the interbody cage comprises a metal cage, a plastic insert, and first and second planar metal pins;
    wherein the metal cage comprises a front slot extending from the front surface towards the center of the interbody cage and wherein the plastic insert is shaped and dimensioned to fit within the front slot;
    wherein the metal cage further comprises a back slot extending from the back surface towards the center of the interbody cage and wherein the first and second planar metal pins are shaped and dimensioned to fit and sit within the back;
    wherein the front slot does not intersect with the back slot;
    inserting and implanting the interbody cage at least partially between a superior vertebra and an inferior vertebra; and
    pushing the first and second planar metal pins from within the back slot towards the front surface of the interbody cage and engaging the vertebral endplates of the superior and inferior vertebras with the first and second planar metal pins, respectively.

13. The method of claim 12, wherein the back slot comprises left and right upwards curved grooves and left and right downwards curved grooves and wherein the first and second planar metal pins comprise left and right sides that are shaped and dimensioned to slide within the left and right upwards curved grooves and the left and right downwards curved grooves, respectively, and wherein the left and right upwards curved grooves do not intersect with the left and right downwards curved grooves.

14. The method of claim 12, wherein the interbody spinal fusion assembly further comprises first and second bone fasteners, and wherein the metal cage further comprises a top through opening extending from the top surface towards the bottom surface and first and second through openings starting in the back surface and extending diagonally towards the top and bottom surfaces, respectively, wherein the first and second through opening are dimensioned to receive the first and second bone fasteners, respectively; and
wherein the method further comprises inserting and screwing the first and second bone fasteners into the vertebral endplates of the superior and inferior vertebras, respectively.

15. The method of claim 12, wherein the interbody spinal fusion assembly further comprises a pin and wherein the position of the plastic insert is secured within the front slot of the metal cage with the pin.

16. The method of claim 12, wherein the top and bottom surfaces of the interbody cage comprise bone engaging teeth.

17. The method of claim 12, wherein each of the first and second planar metal pins comprises an elongated curved body having a trapezoid shaped front end, a rectangular through opening and a central pin, and wherein the central pin extends from the front end of the elongated curved body within the rectangular opening and comprises a distal end projecting in a direction opposite to the curvature of the elongated curved body.

18. The method of claim 17, wherein the metal cage further comprises top and bottom depressions on the top and bottom surfaces, respectively, and wherein the top and bottom depressions are shaped and dimensioned to engage the distal end of the central pin of the first and second planar metal pins, respectively.

19. The method of claim 17, wherein the elongated curved body comprises a back portion with smooth left and right sides, a front portion with teethed left and right sides, and teeth along the left and right edges of the top surface.

20. The method of claim 12, wherein the metal cage comprises one of titanium, stainless steel, biocompatible metal or alloys thereof.

21. The method of claim 12, wherein the first and second planar metal pins comprise one of titanium, stainless steel, biocompatible metal or alloys thereof.

22. The method of claim 12, wherein the plastic insert comprises PEEK.

* * * * *